US012753211B2

(12) United States Patent
Fuqua et al.

(10) Patent No.: US 12,753,211 B2
(45) Date of Patent: Oct. 6, 2026

(54) ANTI-VIRAL COMPOSITIONS AND METHODS OF MAKING AND USING

(71) Applicant: University of Louisville Research Foundation, Inc., Louisville, KY (US)

(72) Inventors: Joshua Fuqua, Pewee Valley, KY (US); Krystal Hamorsky, Owensboro, KY (US); Barry R. O'Keefe, Frederick, MD (US); Tinoush Moulaei, Burlingame, CA (US); Kenneth E. Palmer, Anchorage, KY (US)

(73) Assignees: University of Louisville Research Foundation, Inc., Louisville, KY (US); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 195 days.

(21) Appl. No.: 17/641,264

(22) PCT Filed: Sep. 10, 2020

(86) PCT No.: PCT/US2020/050200
§ 371 (c)(1),
(2) Date: Mar. 8, 2022

(87) PCT Pub. No.: WO2021/050727
PCT Pub. Date: Mar. 18, 2021

(65) Prior Publication Data

US 2022/0289798 A1 Sep. 15, 2022

Related U.S. Application Data

(60) Provisional application No. 62/898,383, filed on Sep. 10, 2019.

(51) Int. Cl.

| | |
|---|---|
| ***C07K 14/405*** | (2006.01) |
| ***A61K 9/00*** | (2006.01) |
| ***A61K 38/16*** | (2006.01) |
| ***A61K 47/10*** | (2017.01) |
| ***C12N 15/82*** | (2006.01) |

(52) U.S. Cl.
CPC .......... *C07K 14/405* (2013.01); *A61K 9/0019* (2013.01); *A61K 9/0031* (2013.01); *A61K 38/168* (2013.01); *A61K 47/10* (2013.01); *C12N 15/8203* (2013.01); *C12N 15/8257* (2013.01)

(58) Field of Classification Search
None
See application file for complete search history.

(56) References Cited

U.S. PATENT DOCUMENTS

| | | | |
|---|---|---|---|
| 8,088,729 | B2 | 1/2012 | O'Keefe |
| 2018/0016307 | A1 | 1/2018 | O'Keefe et al. |

FOREIGN PATENT DOCUMENTS

| | | | |
|---|---|---|---|
| WO | WO 2005/118627 | * | 12/2005 |
| WO | WO 2016/130628 | * | 8/2016 |
| WO | WO2021050727 | | 3/2021 |

OTHER PUBLICATIONS

O'Keefe, B.R. et al., "Broad-Spectrum In Vitro Activity and In Vivo Efficacy of the Antiviral Protein Griffithsin against Emerging Viruses of the Family Coronaviridae," Journal of Virology, vol. 84, p. 5456, 2010.
Kouokam, J., Lasnik, A., and Palmer, K., "Studies in a Murine Model Confirm the Safety of Griffithsin and Advocate Its Further Development as a Microbicide Targeting HIV-1 and Other Enveloped Viruses," Viruses, vol. 8, p. 311, 2016.
Grooms, T.N. et al., "Griffithsin-Modified Electrospun Fibers as a Delivery Scaffold To Prevent HIV Infection." Antimicrobial Agents and Chemotherapy, vol. 60, pp. 6518-6531, Oct. 21, 2016.
Moulaei, Tinoush et al., "Griffithsin tandemers: flexible and potent lectin inhibitors of the human Immunodeficiency virus," Retrovirology, vol. 12, Jan. 23, 2015.
International Search Report and Written Opinion, mailed Feb. 17, 2021—International application No. PCT/US2020/050200; Applicant: Joshua, Fuqua.

* cited by examiner

*Primary Examiner* — Maury A Audet
(74) *Attorney, Agent, or Firm* — Dentons Bingham Greenebaum LLP; Brian W. Chellgren

(57) ABSTRACT

Provided herein are GRFT variants and methods of using such GRFT variants. The GRFT variants described herein can be PEGylated, which significantly improves the pharmacokinetics and decreases the immunogenicity of the GFRT composition.

21 Claims, 20 Drawing Sheets

Specification includes a Sequence Listing.

| | Q | Q 20K | NK | NK 2K | NK 20K | M78K | M78K 2K | M78K 20K | CK | CK 20K |
|---|---|---|---|---|---|---|---|---|---|---|
| EC50 | 8.378 | 33.62 | 15.01 | 60.76 | ~ 52481345 | 11.05 | 33.80 | 304.5 | 10.48 | 90.45 |

| | Q 20K Direct | NK 2K Direct | NK 20K Direct | M78K2K Rx Direct | M78K20K Rx | CK 20K Direct |
|---|---|---|---|---|---|---|
| EC50 | 0.03553 | 0.08746 | 0.01727 | 0.3316 | 0.06239 | 0.02896 |

| | Q 20K | NK 2K | NK 20K | M78K 2K | M78K 20K | CK 20K |
|---|---|---|---|---|---|---|
| EC50 | 16.30 | 7.446 | 26.43 | 10.88 | 19.22 | 14.13 |

ANTI-VIRAL COMPOSITIONS AND METHODS OF MAKING AND USING

CROSS REFERENCE TO RELATED APPLICATIONS

This application claims the benefit of priority under 35 U.S.C. § 119 (e) to U.S. Application No. 62/898,383 filed Sep. 10, 2019. This document is incorporated herein by reference.

REFERENCE TO A SEQUENCE LISTING

This application refers to sequences disclosed in an ASCII file named "2020050200.txt" of 19,474 bytes, created May 12, 2025, incorporated herein by reference.

TECHNICAL FIELD

This disclosure generally relates to anti-viral compositions and methods of making and using such anti-viral compositions.

BACKGROUND

Griffithsin (GRFT) is a lectin originating from the red algae, *Griffithsia*, with potent, broad-spectrum antiviral activity. GRFT effectively inhibits enveloped viruses such as HIV, influenza, HSV-2, and coronaviruses including, without limitation, SARS-COV, MERS and endemic strains, through binding of envelope glycosylation sites. Efforts to improve the potency or stability of GRFT have resulted in the creation of GRFT variants such as Q GRFT, an oxidation resistant variant. GRFT and its variants have been developed primarily for topical delivery due to initial concerns over immunogenicity and pharmacokinetics.

GRFT has the potential, however, to be used systemically in therapeutic applications against multiple other viruses, but requires an improved profile. In its native form, GRFT is not systemically bioavailable following oral delivery and, following parenteral administration, only has a serum half-life of 4-6 hrs. Additionally, anti-GRFT antibodies have been observed in some animal models following systemic and, in some instances, topical delivery.

A systemically available GRFT with improved serum half-life and reduced immunogenicity has the potential to address many unmet clinical.

SUMMARY

GRFT variants and methods of using such GRFT variants are described herein. Such GRFT variants can be PEGylated, which significantly improves the pharmacokinetics and reduces the immunogenicity of the GFRT composition.

In one aspect, mutant GRFT polypeptides including a lysine at at least one amino acid position (e.g., at at least two amino acid positions, at at least three amino acid positions) selected from the group consisting of 1, 5, 24, 61, 64, 78, 80, 81, and 122 (numbered relative to SEQ ID NO: 1) is provided. Representative mutant GRFT polypeptides are shown in SEQ ID NOs: 3-11.

Nucleic acid molecules encoding such mutant GRFT polypeptides also are provided. Representative nucleic acid molecules encoding such mutant GRFT polypeptides are shown in SEQ ID NO: 12-21. In another aspect, vectors that include a nucleic acid molecule as described herein are provided. In still another aspect, host cells including a nucleic acid molecule or a vector as described herein are provided.

In some embodiments, the mutant GRFT polypeptides described herein include, or further include, PEG. In other words, the mutant GRFT polypeptides described herein can be PEGylated.

In some embodiments, the mutant GRFT polypeptides described herein further include a therapeutic moiety. Representative therapeutic moieties include, without limitation, an anti-viral, an anti-microbial, a drug, a small molecule, a therapeutic protein, a nanoparticle, and an enzyme.

In yet another aspect, therapeutic compositions are provided that include the mutant GRFT polypeptides described herein and a pharmaceutically acceptable carrier. In some embodiments, such a therapeutic composition can further include a therapeutic moiety. Representative therapeutic moieties include, without limitation, an anti-viral, an anti-microbial, a drug, a small molecule, a therapeutic protein, a nanoparticle, and an enzyme. In some embodiments, the therapeutic moiety is covalently attached to the mutant GRFT polypeptide.

In yet another aspect, methods of systemically treating a viral infection in an individual are provided. Typically, such a method includes administering a mutant GRFT polypeptide as described herein to the individual. Representative viral infections include, without limitation, human immunodeficiency virus (HIV), severe acute respiratory syndrome (SARS), coronavirus (SARS-COV), influenza, herpes simplex virus (HSV), Japanese encephalitis virus, hepatitis C (HEPC), Middle East Respiratory Syndrome (MERS), and Nipah virus (NiV). In some embodiments, the administering step includes intraperitoneal (ip), intravenously (iv), subcutaneous, intranasal, intrarectal or sublingual routes.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

Figure 1:
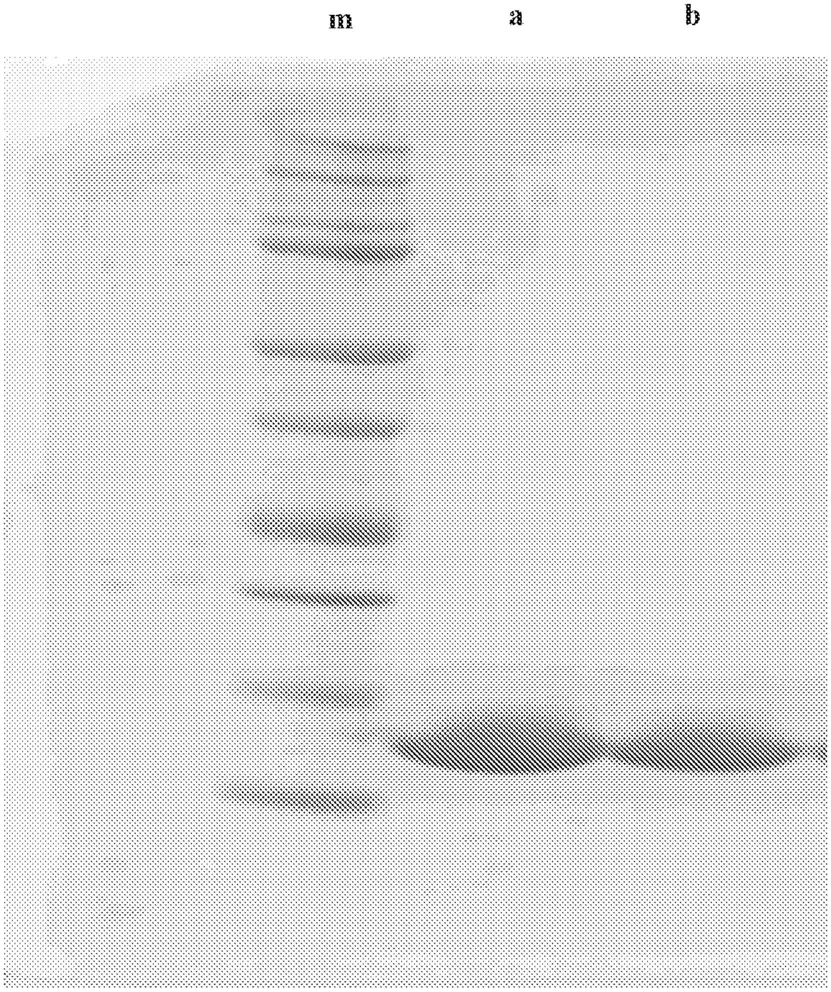
FIG. 1 is an SDS gel that shows the purified product of Q GRFT (lane a) and -K (lane b) constructs (and a marker lane (m)). The gel was stained using Coomassie blue and destained for imaging. Each well contained 10 μg of sample in 15 μl per well.

There has been particular interest in expanding the delivery platform of GRFT beyond topical, particularly to achieve efficacious delivery via systemic administration.

Conjugating at least one binding partner to the surface of GRFT can extend the half-life of GRFT and protect its immunogenic epitopes, thereby modifying the systemic profile of GRFT. Binding partners can include, without limitation, polyethylene glycol (PEG), human serum albumin, or antibody fragments. Generating a binding partner-modified GRFT can produce a systemically available viral therapeutic that fills existing gaps in the current treatment paradigms of multiple viruses.

The most popular conjugation mechanism is primary amine coupling, which works through either a lysine or amino terminal amino acid. Conjugation, however, can be difficult to direct and heterogeneity in the position and extent of binding can lead to difficulty characterizing, comparing and standardizing the degree of conjugation. Therefore, the arrangement of lysines within GRFT can be engineered to optimize or control the position at which the binding partner is conjugated.

The Q GRFT (SEQ ID NO:1) molecule contains a lysine at position 7 and a lysine at position 100. These lysines, however, are not readily available due to steric hindrance, and using them for conjugation would result in low yields. Before modifying the location of lysines within GRFT to preferred sites for amine coupling, we first wanted to remove lysine completely from GRFT (i.e., create a lysine-free GRFT; "-K GRFT") and then evaluate its characteristics. As described herein, -K GRFT is expressed well, can be purified using standard chromatography, and retains similar activity, structure, and stability to Q GRFT.

Lysine residues then can be added back into-K GRFT at desired positions and the impact on conjugation efficiency and protein function can be tested. Using structure-guided engineering, sites at which lysines can be introduced were identified by focusing on available arginines (R) and methionines (M) as well as an addition at each of the amino (N)- and carboxy (C)-terminal ends. For example, an amino acid residue at any one or more of the following positions can be mutated to lysine (numbered relative to Q GRFT shown in SEQ ID NO:1): the N-terminal end ("NK"), position 5 (R5K), position 24 (R24K), position 61 (M61K), position 64 (R64K), position 78 (M78K), position 80 (R80K), position 81 (R81K), or at the C-terminal end (CK). Representative mutant GRFT protein sequences, also referred to as GRFT variants, are shown in SEQ ID NOs: 3-11.

A lysine can be introduced at one, two, three or more of the indicated positions. Representative double mutations include, without limitation, M78K and CK; R81K and CK; and M78K and R81K; and representative triple mutations include, without limitation, NK, M78K and CK; R5K, M61K and R80K; R24K, R64K and R81K. As described herein, mutants can be evaluated using Western Blot and SDS-PAGE to verify expression, size and purity; Gp120 ELISA and TSA to demonstrate binding capability and thermal stability; and retention time on SEC to evaluate, e.g., size (e.g., dimerization) and purity.

A mutant GRFT protein as described herein can be encoded by a mutant GRFT nucleic acid. Representative mutant GRFT nucleic acid sequences are shown in SEQ ID NOs: 12-21.

Polypeptides are provided herein (see, for example, SEQ ID NOs: 3-11), as are the nucleic acids encoding such polypeptides (see, for example, SEQ ID NOs: 12-21). Also provided are polypeptides and nucleic acids that differ from SEQ ID NOs: 3-11 and SEQ ID NOs: 12-21, respectively. Polypeptides and nucleic acids that differ in sequence from SEQ ID NOs: 3-11 and SEQ ID NOs: 12-21, respectively, can have at least 80% sequence identity (e.g., at least 85%, at least 90%, at least 95%, at least 96%, at least 97%, at least 98%, or at least 99% sequence identity) to SEQ ID NOs: 3-11 and SEQ ID NOs: 12-21, respectively.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the algorithm described by Altschul et al. (1997, Nucleic Acids Res., 25:3389 3402) as incorporated into BLAST (Basic Local Alignment Search Tool) programs, available at ncbi.nlm-.nih.gov on the World Wide Web. BLASTN is the program used to align and compare the identity between nucleic acid sequences, while BLASTP is the program used to align and compare the identity between amino acid sequences. When utilizing BLAST programs to calculate the percent identity between a sequence and another sequence, the default parameters of the respective programs generally are used.

A skilled artisan will appreciate that changes can be introduced into a nucleic acid molecule (e.g., SEQ ID NOs: 12-21), thereby leading to changes in the amino acid sequence of the encoded polypeptide. For example, changes can be introduced into nucleic acid sequences using mutagenesis (e.g., site-directed mutagenesis, PCR-mediated mutagenesis) or by chemically synthesizing a nucleic acid molecule having such changes. In some instances, a polypeptide can be chemically synthesized to contain one or more mutations.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). In addition, an isolated nucleic acid molecule can include an engineered nucleic acid molecule such as a recombinant or a synthetic nucleic acid molecule.

As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the proteins and naturally occurring molecules with which it is naturally associated. Since a polypeptide that is chemically synthesized is, by nature, separated from the components that naturally accompany it, a synthetic polypeptide is "purified."

A nucleic acid molecule can be introduced into a vector (e.g., a cloning vector, or an expression vector) for convenience of manipulation or to generate a polypeptide. Vectors, including expression vectors, are commercially available or can be produced by recombinant DNA techniques routine in the art. A vector containing a nucleic acid can have expression elements (e.g., nucleic acid sequences that direct and regulate expression of nucleic acid coding sequences such as, e.g., promoters, introns, enhancer sequences, response elements, or inducible elements) operably linked to such a nucleic acid, and further can include sequences such as those encoding a selectable marker (e.g., an antibiotic resistance gene). As used herein, operably linked means that a promoter or other expression element(s) are positioned in a vector relative to a nucleic acid in such a way as to direct or regulate expression of the nucleic acid (e.g., in-frame). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used, for example, in purification of the encoded polypeptide (e.g., 6×His tag, glutathione S-transferase (GST)).

Vectors as described herein can be introduced into a host cell. As used herein, "host cell" refers to the particular cell into which the nucleic acid is introduced and also includes the progeny or potential progeny of such a cell. A host cell can be any prokaryotic or eukaryotic cell. For example, nucleic acids can be expressed in bacterial cells such as *E. coli*, or in insect cells, yeast or mammalian cells (such as Chinese hamster ovary cells (CHO) or COS cells). Other suitable host cells are known to those skilled in the art. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

Nucleic acids can be detected using any number of amplification techniques (see, e.g., PCR Primer: A Laboratory Manual, 1995, Dieffenbach & Dveksler, Eds., Cold Spring Harbor Laboratory Press, Cold Spring Harbor, NY; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid. Nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY; Sections 7.37-7.57, 9.47-9.57, 11.7-11.8, and 11.45-11.57).

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed. Detection (e.g., of a nucleic acid amplification product, a hybridization complex, or a polypeptide) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

As described herein, the addition of a binding partner to GRFT can significantly improve the pharmacokinetics and significantly reduce the immunogenicity. While the binding partner exemplified herein is PEG, those skilled in the art would appreciate that other binding partners (e.g., human serum albumin or antibody fragments) can be used in a similar manner. PEG is a well-known polymer of ethylene oxide and are available over a range of molecular weights, ranging from 300 g/mol to 10,000,000 g/mol. PEG polymers suitable for use herein typically include 1,000 MW-200,000 MW PEG (e.g., 2,500 MW-175,000 MW; 5,000 MW-150,000 MW; 7,500 MW-100,000 MW; 10,000 MW-75,000 MW; 15,000 MW-50,000 MW; or 20,000 MW-40,000 MW) in an amount such that each GRFT molecule, which is a dimer, is conjugated to at least one PEG polymer.

Any of the GRFT variants described herein (e.g., any of the PEGylated GRFT variants described herein) can be used in a therapeutic composition. In addition to the GRFT variants described herein (e.g., the PEGylated GRFT variants described herein), therapeutic compositions generally include a pharmaceutically acceptable carrier. As used herein, "pharmaceutically acceptable carrier" is intended to include solvents (e.g., a sterile diluent such as water for injection, saline solution (e.g., phosphate buffered saline (PBS)), fixed oils, a polyol (for example, glycerol, propylene glycol, and liquid polyetheylene glycol, and the like), glycerine, or other synthetic solvents), dispersion media, coatings, antibacterial and anti-fungal agents (e.g., parabens, chlorobutanol, phenol, ascorbic acid, thimerosal, and the like), and/or isotonic and absorption delaying agents (e.g., isotonic agents, for example, sugars, polyalcohols (e.g., mannitol or sorbitol), sodium chloride, aluminum monostearate and gelatin) that are compatible with pharmaceutical administration. Except insofar as any conventional media or agent is incompatible with the GRFT variants described herein, use thereof in the compositions is contemplated.

In some instances, it may be desirable to attach a therapeutic moiety to the surface of the GRFT variant. Therapeutic moieties are known in the art and can include, without limitation, anti-virals, anti-microbials, drugs, small molecules, therapeutic proteins (e.g., antibodies), nanoparticles and enzymes. Methods of attaching a therapeutic moiety to the surface of a GRFT variant are known in the art. See, for example, Belen et al., 2019, Front. Pharmacol., 10:1450).

The compositions described herein (e.g., one or more GRFT variants containing one or more of the mutations described herein) can be provided in an article of manufacture (e.g., a kit). In some instances, the one or more GRFT variants can be PEGylation; in some instances, PEG can be included in the article of manufacture. Article of manufacture are known in the art and can include, without limitation, one or more containers, vials, tubes, ampoules, or syringes made of glass or plastic, and also can contain a package insert or package label having instructions thereon for PEGylating the GRFT variants and/or for using the GRFT variants. Articles of manufacture may additionally include reagents for carrying out such methods (e.g., buffers, enzymes, or co-factors).

A therapeutic composition containing one or more of the GRFT variants described herein (e.g., one or more of the PEGylated GRFT variants described herein) can be used to systemically treat a viral infection in an individual. As described herein, one or more of the GRFT variants (e.g., one or more of the PEGylated GRFT variants) can be administered to an individual suspected of having or who has been diagnosed with having a viral infection. As discussed herein, the PEGylated GRFT variants are intended to be systemically bioactive when delivered to an individual. Therefore, it would be understood that administration can include, without limitation, parenteral, e.g., intravenous, intradermal, subcutaneous, sublingual, transmucosal, intranasal, and intrarectal.

The methods described herein are suitable for treating any number of viral infections in a subject including, without limitation, human immunodeficiency virus (HIV), severe acute respiratory syndrome (SARS), coronavirus (SARS-COV-2), influenza, herpes simplex virus (HSV), Japanese encephalitis virus, hepatitis C virus (HCV), Middle East Respiratory Syndrome (MERS), and Nipah virus (NiV). Since treatments and/or vaccines against many of these viruses are lacking or not available, the GRFT variants described herein can be used as a short-term prophylactic and/or a treatment for infections (e.g., breakthrough infections), and could be used in high risk populations.

The therapeutic compositions described herein can be formulated in dosage unit form for ease of administration and uniformity of dosage. Dosage unit form as used herein refers to physically discrete units suited as unitary dosages for a subject to be treated; each unit containing a predetermined quantity of one or more of the GRFT variants described herein calculated to produce the desired therapeutic effect in association with the pharmaceutical carrier. The dosage unit forms are dependent upon the desired amount of the one or more GRFT variants, and can be formulated in a single dose or in multiple doses. Treatment of a subject may require administration of a single dose or may require repeated doses.

As used herein, the term "treat", "treating" or "treatment" of any disease or disorder refers to modulating or ameliorating the disease or disorder (i.e., slowing or arresting or reducing the development or progression of the disease or at least one of the clinical symptoms thereof). In another embodiment, "treat", "treating" or "treatment" refers to alleviating or ameliorating at least one physical parameter (e.g., viral load). In yet another embodiment, "treat", "treating" or "treatment" refers to preventing or delaying the onset or development or progression of the disease or disorder.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Mutagenesis

-K GRFT was designed by replacing lysines at positions 7 and 100 in the Q-GRFT amino acid sequence with arginines.

```
Q GRFT
                                          (SEQ ID NO: 1)
MSLTHRKFGG SGGSPFSGLS SIAVRSGSYL DAIIIDGVHH

GGSGGNLSPT FTFGSGEYIS NMTIRSGDYI DNISFETNQG

RRFGPYGGSG GSANTLSNVK VIQINGSAGD YLDSLDIYYE

QY

-K GRFT
                                          (SEQ ID NO: 2)
MSLTHRRFGG SGGSPFSGLS SIAVRSGSYL DAIIIDGVHH

GGSGGNLSPT FTFGSGEYIS NMTIRSGDYI DNISFETNQG

RRFGPYGGSG GSANTLSNVR VIQINGSAGD YLDSLDIYYE

QY
```

Example 2—Expression

Figure 2:
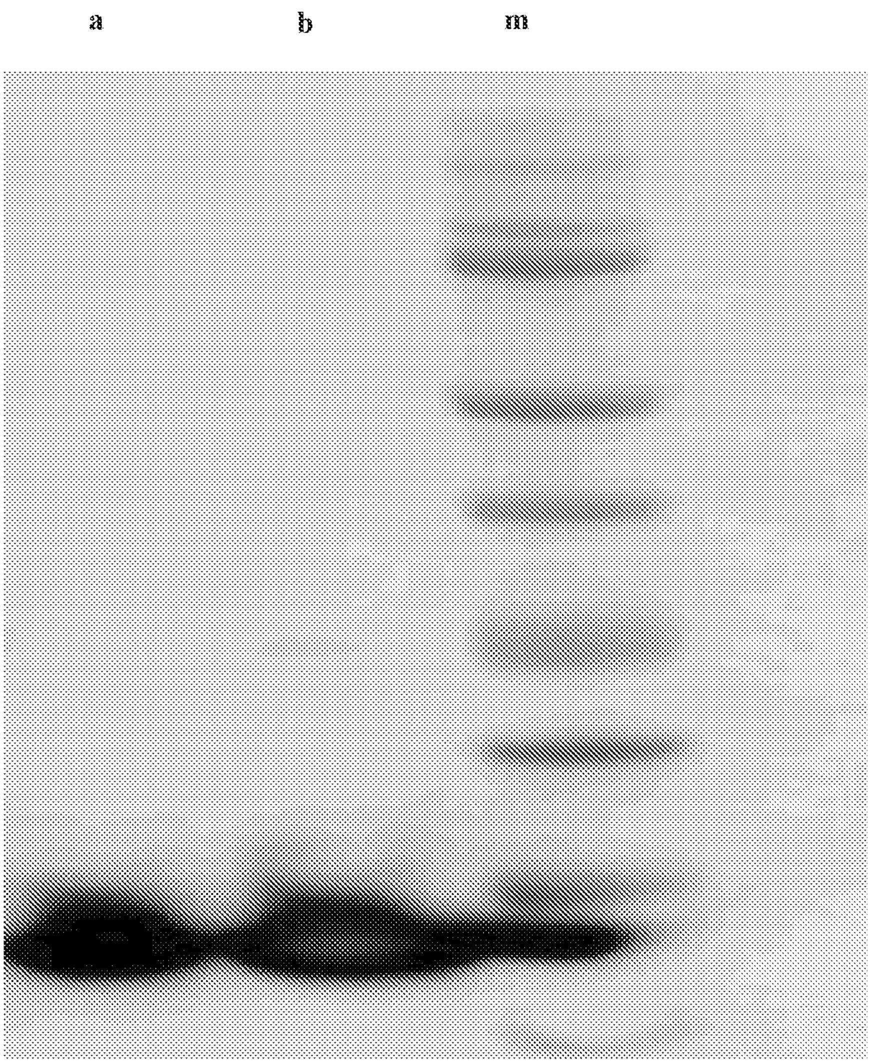
FIG. 2 is a Western Blot of Q GRFT (lane a) and -K (lane b) (and a marker lane (m)). Each well contained 2 μg of sample in 15 μl per well.

*Nicotiana benthamiana* plants were inoculated with infectious TMV virions encoding-K GRFT or Q GRFT sequences. After two weeks, all plants exhibiting signs of infection were harvested, and the proteins were extracted and purified using filtration methods, Multi Modal Chromatography, and Reversed Phase Chromatography. Samples were analyzed by SDS-PAGE, which demonstrated that-K GRFT has a similar size to Q GRFT (FIG. 1), and Western Blot, which indicated that-K GRFT is similar in size to Q GRFT and is detectable with anti GRFT antibody (FIG. 2).

Example 3—Purification

Infected plant material was processed through a two-step filter process and a two-step chromatography process. In the first filtration step, plant material was blended with 100 mM sodium acetate+300 mM sodium chloride+20 mM ascorbic acid+10 mM sodium meta-bisulfite (pH 4.0), and filtered through two layers of cheese cloth and miracloth. The pH of the sample remained at 4; the sample was then heated to 55° C. and filter aid added. Plant juice was extracted through a 1.0 μm filter press, and then bentonite was added overnight and the juice was filter pressed again with 0.3 μm pads. Once this was done, the clarified juice was passed through a 0.2 μm filter to be clarified even further and then loaded into the ÄKTA pure for chromatography purification.

Filtered clarified plant juice was processed through a two-step chromatography process. The first step was multimodal chromatography (MMC) using buffers 20 mM NaAc (pH 4) and 1×PBS (pH 7.4). The second step was reversed-phase chromatography (RPC) using buffers 20 mM $NaPO_4$ (pH 6) and 20 mM $NaPO_4$+15% n-propanol (pH 6). Next, the purified protein was diluted with 1×PBS and filtered using ultrafiltration and diafiltration (UFDF). This step allowed protein to be concentrated. Afterwards, nano drop test results and coefficient extinction factors were used to determine the final concentration.

Example 4—Characterization

Figure 3:
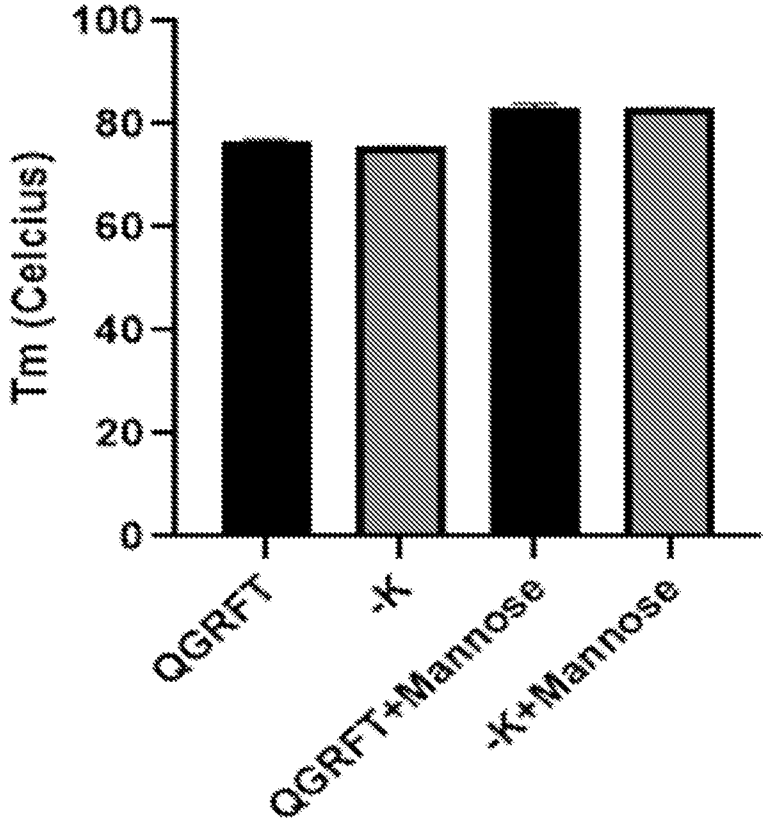
FIG. 3 is a graph showing the results of Thermal Shift Assays (TSAs), which were run to determine the melting point ligand binding capacity. TSA was ran with and without 20 mM mannose. Data was analyzed by t-test.

-K was characterized using Thermal Shift Assays (TSAs) (FIG. 3). Melting temperatures were calculated with and without the presence of mannose (FIG. 3 and Table 1). Stabilization of the protein in the presence of mannose (higher melt temp) indicates binding of the sugar and retained activity of the protein. TSA data shows that-K was able to maintain a binding temperature that is very close to Q GRFT, and also was as thermally stable as Q-GRFT at high temperatures.

Figure 4:
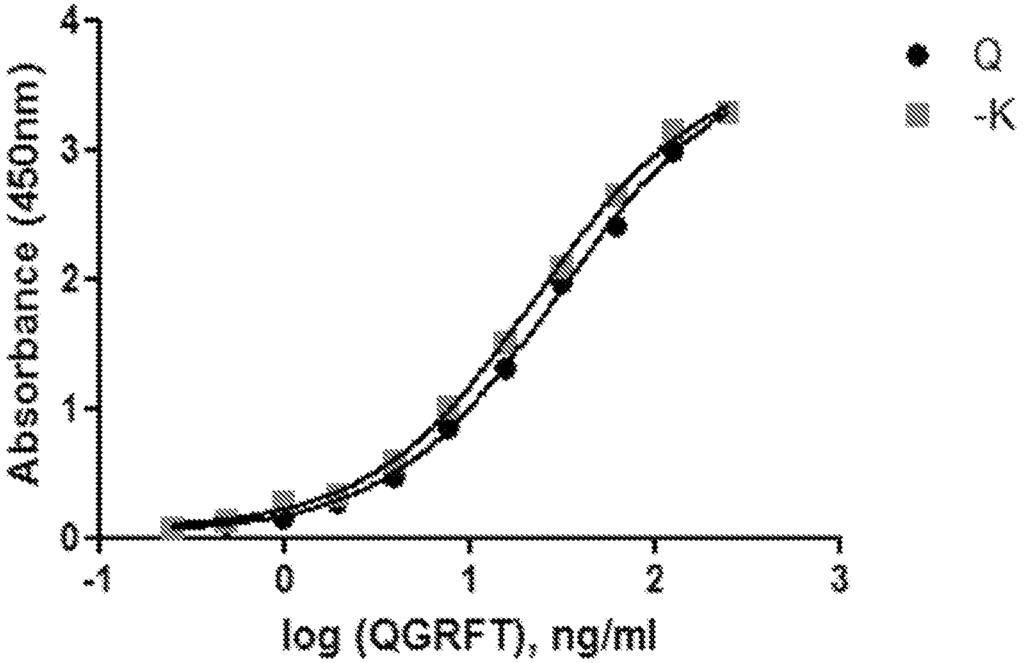
FIG. 4 is a graph showing GP120 ELISA, which was run to determine the activity of -K compared to Q GRFT. -K and Q GRFT were run in triplicate and analyzed by t-test.

-K also was characterized using an ELISA gp120 binding assay (FIG. 4 and Table 2). The EC50 values obtained from these experiments demonstrate that-K has similar activity to Q GRFT on gp120 (FIG. 4 and Table 2).

TABLE 1

| Type | Tm | Tm w/Mannose |
|---|---|---|
| Q GRFT | 76.89 ± 0.2524 | 83.44 ± 0.3906 |
| -K GRFT | 75.58 ± 0.07700 | 83.09 ± 0.1540 |

TABLE 2

| Type | EC50 Value |
|---|---|
| Q GRFT | 30.49 ± 0.0358 |
| -K GRFT | 22.97 ± 0.02787 |

Figure 5A:
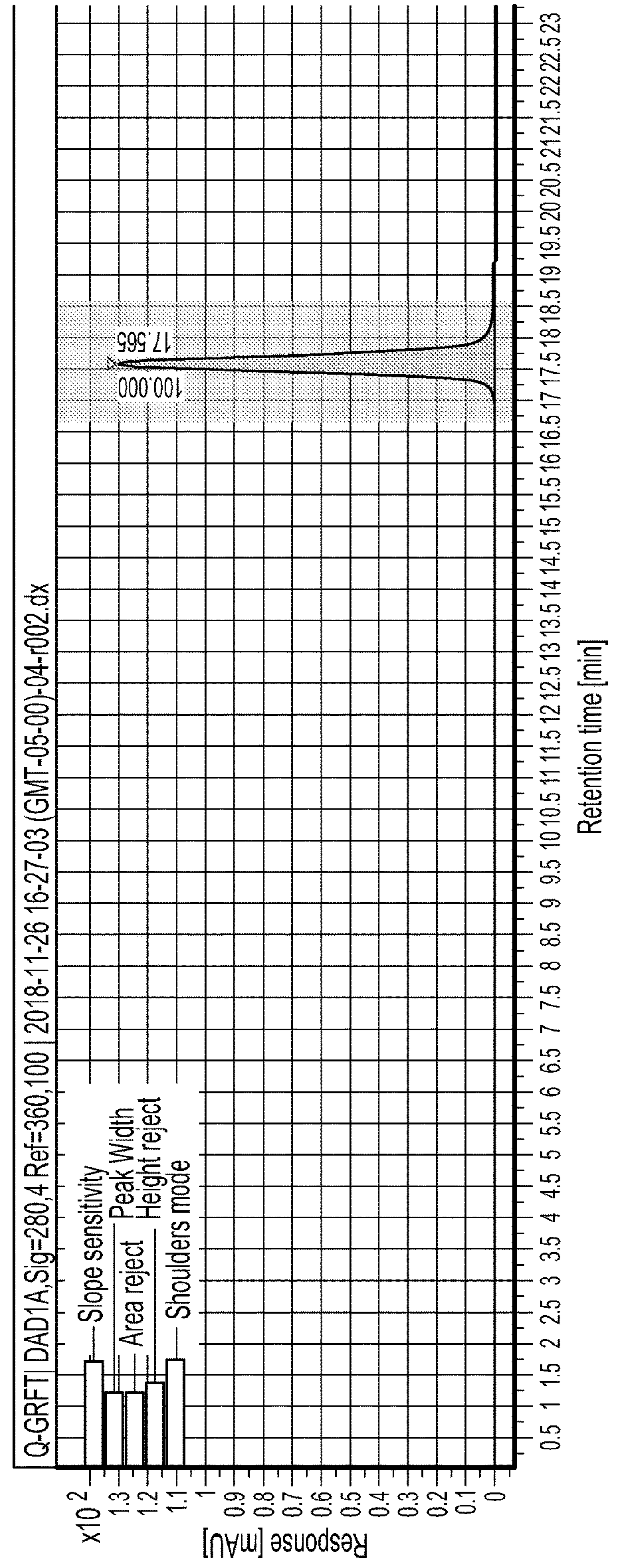
FIG. 5A-5B show Q GRFT (FIG. 5A) and -K GRFT (FIG. 5B) run on size exclusion chromatography (SEC) to determine the retention rate to be able to extrapolate the size of the molecule.
Figure 5B:
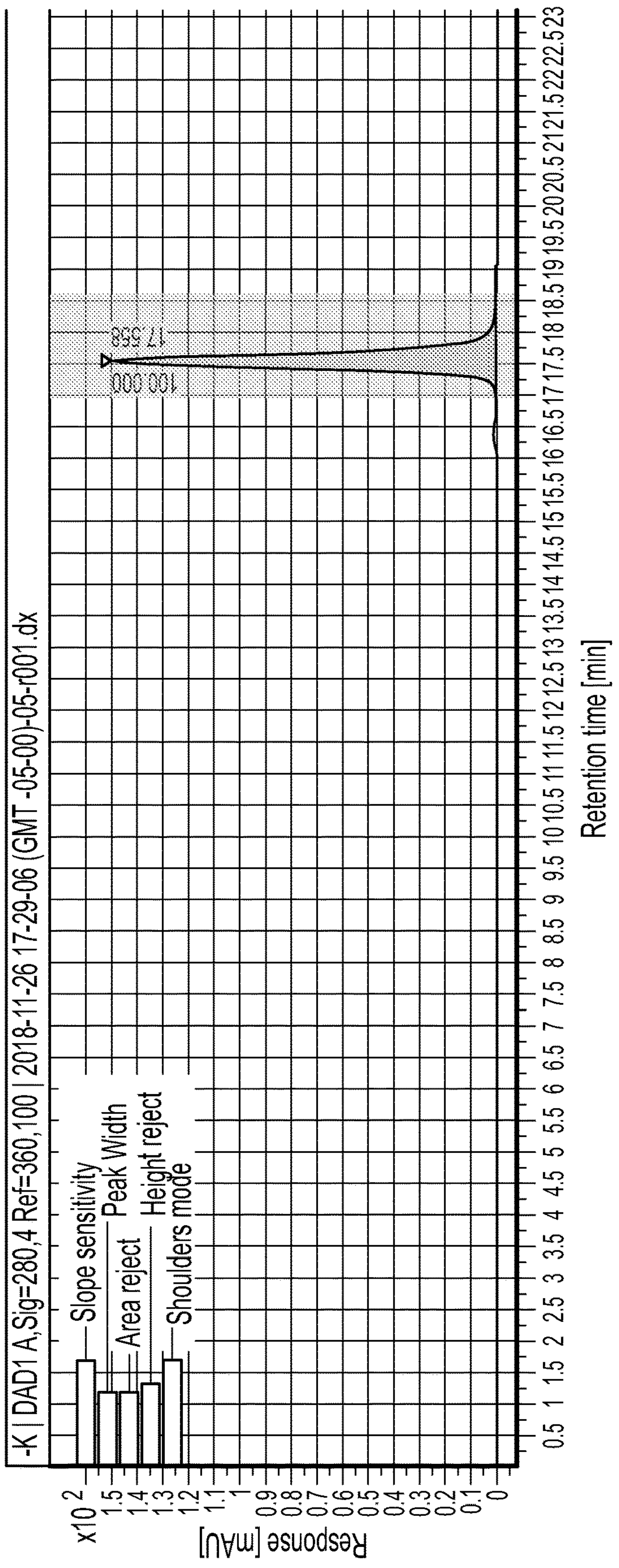

-K GRFT was additionally characterized using size exclusion chromatography (SEC) (FIGS. 5A and 5B). -K GRFT had a similar retention time as Q GRFT, which indicates a similar size. The SEC also showed the purity of the -K GRFT product was high.

Figure 5C:
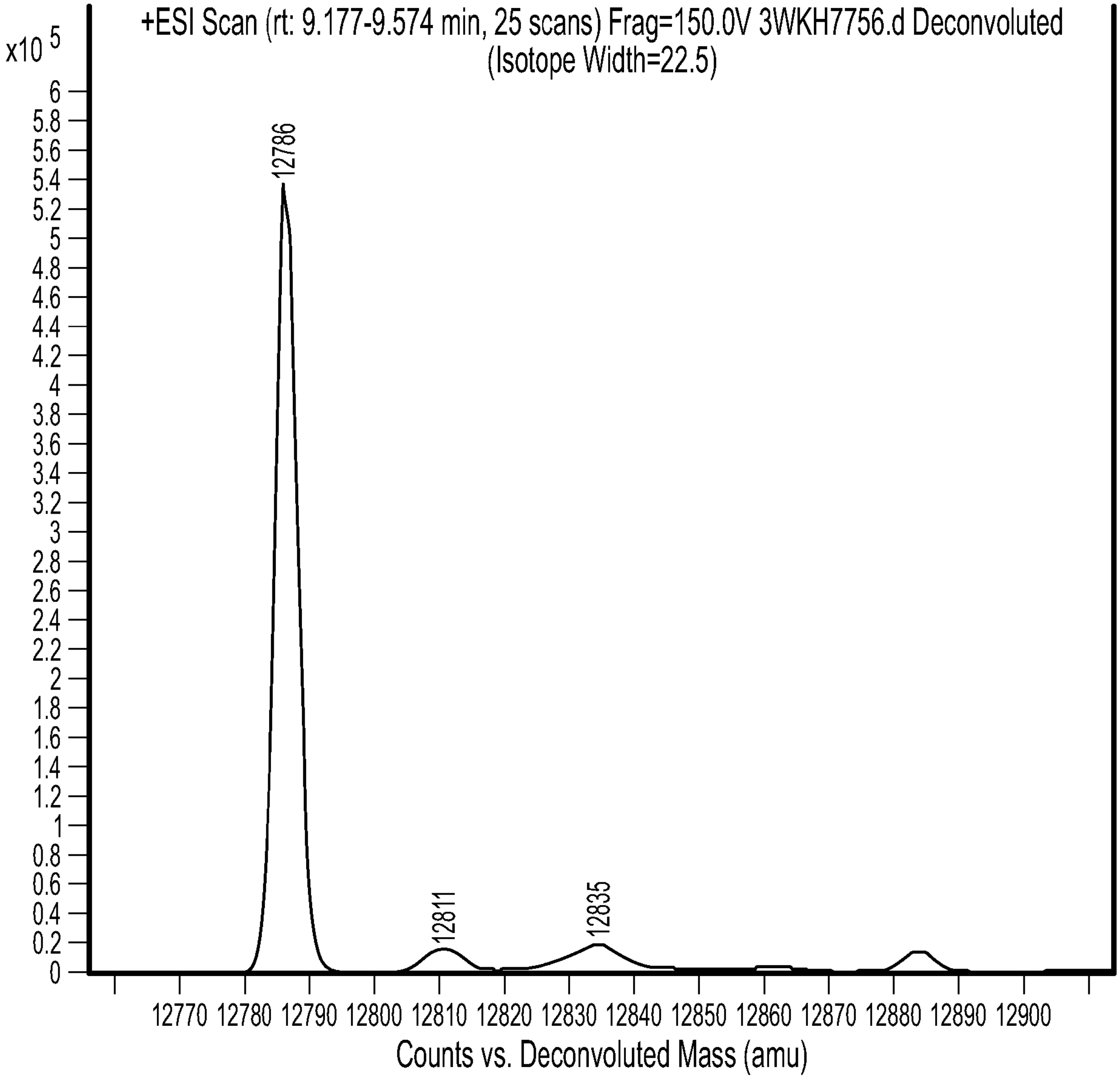
FIG. 5C is a tracing from mass spectroscopy run on Q GRFT and -K GRFT. Samples for mass spectroscopy were made at 1 mg/mL in 100 μl total.

Results of mass spectroscopy (FIG. 5C) showed that -K GRFT has a molecular size of 12,786 atomic mass unit (amu), which is essentially identical to the predicted value of 12,785.7881 amu. In addition, the size of -K GRFT is very similar to that of Q GRFT, which has a molecular weight of 12,734 amu.

In summary, -K GRFT retains similar properties as Q GRFT (e.g., size, melting temperature, activity and thermal stability) after being expressed, purified and characterized. Therefore, -K GRFT is active and stable. Although lysine is important for the molecule, its activity and capacity was not negatively effected by its removal. Based on these results, modifying the lysine content of GRFT did not affect its characteristics.

Example 5—PEGylated Q GRFT

In order to control conjugation, GRFT variants were made that had alternative lysine residues available for conjugation. These variants were (NK, R5K, R24K, M61K, R64K, M78K, R80K, R81K, CK) and two controls (Q and-K). The mutation position in each of these variants was numbered after the initial methionine was cleaved. As such, the lysine "K" of the R5K mutation at position 5 (ignoring the methionine) is adjacent the arginine "R" introduced by the -K mutation at position 7 (counting the methionine), as shown in SEQ ID NO: 4.

```
-K CK
                                                           (SEQ ID NO: 3)
MSLTHRRFGG SGGSPFSGLS SIAVRSGSYL DAIIIDGVHH GGSGGNLSPT FTFGSGEYIS NMTIRSGDYI

DNISFETNQG RRFGPYGGSG GSANTLSNVR VIQINGSAGD YLDSLDIYYE QYK

-K R5K
                                                           (SEQ ID NO: 4)
MSLTHKRFGG SGGSPFSGLS SIAVRSGSYL DAIIIDGVHH GGSGGNLSPT FTFGSGEYIS NMTIRSGDYI

DNISFETNQG RRFGPYGGSG GSANTLSNVR VIQINGSAGD YLDSLDIYYE QY

-K R24K
                                                           (SEQ ID NO: 5)
MSLTHRRFGG SGGSPFSGLS SIAVKSGSYL DAIIIDGVHH GGSGGNLSPT FTFGSGEYIS NMTIRSGDYI

DNISFETNQG RRFGPYGGSG GSANTLSNVR VIQINGSAGD YLDSLDIYYE QY

-K M61K
                                                           (SEQ ID NO: 6)
MSLTHRRFGG SGGSPFSGLS SIAVRSGSYL DAIIIDGVHH GGSGGNLSPT FTFGSGEYIS NKTIRSGDYI

DNISFETNQG RRFGPYGGSG GSANTLSNVR VIQINGSAGD YLDSLDIYYE QY

-K R64K
                                                           (SEQ ID NO: 7)
MSLTHRRFGG SGGSPFSGLS SIAVRSGSYL DAIIIDGVHH GGSGGNLSPT FTFGSGEYIS NMTIKSGDYI

DNISFETNQG RRFGPYGGSG GSANTLSNVR VIQINGSAGD YLDSLDIYYE QY

-K M78K
                                                           (SEQ ID NO: 8)
MSLTHRRFGG SGGSPFSGLS SIAVRSGSYL DAIIIDGVHH GGSGGNLSPT FTFGSGEYIS NMTIRSGDYI

DNISFETNKG RRFGPYGGSG GSANTLSNVR VIQINGSAGD YLDSLDIYYE QY
```

-continued

-K R80K (SEQ ID NO: 9)

MSLTHRRFGG SGGSPFSGLS SIAVRSGSYL DAIIIDGVHH GGSGGNLSPT FTFGSGEYIS NMTIRSGDYI

DNISFETNQG KRFGPYGGSG GSANTLSNVR VIQINGSAGD YLDSLDIYYE QY

-K R81K (SEQ ID NO: 10)

MSLTHRRFGG SGGSPFSGLS SIAVRSGSYL DAIIIDGVHH GGSGGNLSPT FTFGSGEYIS NMTIRSGDYI

DNISFETNQG RKFGPYGGSG GSANTLSNVR VIQINGSAGD YLDSLDIYYE QY

-K NK (SEQ ID NO: 11)

MKSLTHRRFGG SGGSPFSGLS SIAVRSGSYL DAIIIDGVHH GGSGGNLSPT FTFGSGEYIS NMTIRSGDYI

DNISFETNQG RRFGPYGGSG GSANTLSNVR VIQINGSAGD YLDSLDIYYE QY

-K (SEQ ID NO: 12)

ATGTCACTTACACATCGAAGATTCGGTGGTAGCGGCGGGAGTCCATTCTCCGGACTCAGTTCAATAGCAGTGCGATCTGGC

TCTTATCTGGATGCTATCATAATCGACGGCGTGCACCATGGAGGCTCCGGCGGCAATCTCTCCCCCACTTTCACTTTCGGC

TCTGGAGAGTACATATCCAATATGACAATTAGAAGTGGCGACTATATCGACAATATCTCATTCGAAACCAACCAGGGTCGG

CGGTTTGGGCCATATGGAGGATCCGGTGGAAGCGCTAACACACTCAGTAATGTTCGAGTAATCCAGATTAACGGCTCCGCG

GGGGATTACTTGGATTCCCTGGACATATATTATGAGCAGTATTGA

-K CK (SEQ ID NO: 13)

ATGTCACTTACACATCGAAGATTCGGTGGTAGCGGCGGGAGTCCATTCTCCGGACTCAGTTCAATAGCAGTGCGATCTGGC

TCTTATCTGGATGCTATCATAATCGACGGCGTGCACCATGGAGGCTCCGGCGGCAATCTCTCCCCCACTTTCACTTTCGGC

TCTGGAGAGTACATATCCAATATGACAATTAGAAGTGGCGACTATATCGACAATATCTCATTCGAAACCAACCAGGGTCGG

CGGTTTGGGCCATATGGAGGATCCGGTGGAAGCGCTAACACACTCAGTAATGTTCGAGTAATCCAGATTAACGGCTCCGCG

GGGGATTACTTGGATTCCCTGGACATATATTATGAGCAGTATAAATGA

-K R5K (SEQ ID NO: 14)

ATGTCACTTACACATAAAAGATTCGGTGGTAGCGGCGGGAGTCCATTCTCCGGACTCAGTTCAATAGCAGTGCGATCTGGC

TCTTATCTGGATGCTATCATAATCGACGGCGTGCACCATGGAGGCTCCGGCGGCAATCTCTCCCCCACTTTCACTTTCGGC

TCTGGAGAGTACATATCCAATATGACAATTAGAAGTGGCGACTATATCGACAATATCTCATTCGAAACCAACCAGGGTCGG

CGGTTTGGGCCATATGGAGGATCCGGTGGAAGCGCTAACACACTCAGTAATGTTCGAGTAATCCAGATTAACGGCTCCGCG

GGGGATTACTTGGATTCCCTGGACATATATTATGAGCAGTATTGA

-K R24K (SEQ ID NO: 15)

ATGTCACTTACACATCGAAGATTCGGTGGTAGCGGCGGGAGTCCATTCTCCGGACTCAGTTCAATAGCAGTGAAGTCTGGC

TCTTATCTGGATGCTATCATAATCGACGGCGTGCACCATGGAGGCTCCGGCGGCAATCTCTCCCCCACTTTCACTTTCGGC

TCTGGAGAGTACATATCCAATATGACAATTAGAAGTGGCGACTATATCGACAATATCTCATTCGAAACCAACCAGGGTCGG

CGGTTTGGGCCATATGGAGGATCCGGTGGAAGCGCTAACACACTCAGTAATGTTCGAGTAATCCAGATTAACGGCTCCGCG

GGGGATTACTTGGATTCCCTGGACATATATTATGAGCAGTATTGA

-K M61K (SEQ ID NO: 16)

ATGTCACTTACACATCGAAGATTCGGTGGTAGCGGCGGGAGTCCATTCTCCGGACTCAGTTCAATAGCAGTGCGATCTGGC

TCTTATCTGGATGCTATCATAATCGACGGCGTGCACCATGGAGGCTCCGGCGGCAATCTCTCCCCCACTTTCACTTTCGGC

TCTGGAGAGTACATATCCAATAAGACAATTAGAAGTGGCGACTATATCGACAATATCTCATTCGAAACCAACCAGGGTCGG

CGGTTTGGGCCATATGGAGGATCCGGTGGAAGCGCTAACACACTCAGTAATGTTCGAGTAATCCAGATTAACGGCTCCGCG

GGGGATTACTTGGATTCCCTGGACATATATTATGAGCAGTATTGA

-continued

-K R64K (SEQ ID NO: 17)

ATGTCACTTACACATCGAAGATTCGGTGGTAGCGGCGGGAGTCCATTCTCCGGACTCAGTTCAATAGCAGTGCGATCTGGC

TCTTATCTGGATGCTATCATAATCGACGGCGTGCACCATGGAGGCTCCGGCGGCAATCTCTCCCCCACTTTCACTTTCGGC

TCTGGAGAGTACATATCCAATATGACAATTAAGAGTGGCGACTATATCGACAATATCTCATTCGAAACCAACCAGGGTCGG

CGGTTTGGGCCATATGGAGGATCCGGTGGAAGCGCTAACACACTCAGTAATGTTCGAGTAATCCAGATTAACGGCTCCGCG

GGGGATTACTTGGATTCCCTGGACATATATTATGAGCAGTATTGA

-K M78K (SEQ ID NO: 18)

ATGTCACTTACACATCGAAGATTCGGTGGTAGCGGCGGGAGTCCATTCTCCGGACTCAGTTCAATAGCAGTGCGATCTGGC

TCTTATCTGGATGCTATAATTATCGACGGAGTACATCACGGGGGGTCTGGGGGAAATCTTTCACCGACTTTTACATTTGGA

TCCGGCGAATACATTTCTAATATGACCATTAGGTCCGGAGACTACATCGATAACATTAGCTTCGAAACGAACAAGGGGCGG

CGCTTTGGACCCTATGGTGGCAGCGGTGGCAGCGCCAACACCCTCAGCAACGTCAGAGTGATCCAGATCAATGGCAGCGCC

GGGGACTACCTGGATAGCCTGGACATCTATTACGAGCAGTACTGA

-K R80K (SEQ ID NO: 19)

ATGTCACTTACACATCGAAGATTCGGTGGTAGCGGCGGGAGTCCATTCTCCGGACTCAGTTCAATAGCAGTGCGATCTGGC

TCTTATCTGGATGCTATCATAATCGACGGCGTGCACCATGGAGGCTCCGGCGGCAATCTCTCCCCCACTTTCACTTTCGGC

TCTGGAGAGTACATATCCAATATGACAATTAGAAGTGGCGACTATATCGACAATATCTCATTCGAAACCAACCAGGGTAAA

CGGTTTGGGCCATATGGAGGATCCGGTGGAAGCGCTAACACACTCAGTAATGTTCGAGTAATCCAGATTAACGGCTCCGCG

GGGGATTACTTGGATTCCCTGGACATATATTATGAGCAGTATTGA

-K R81K (SEQ ID NO: 20)

ATGTCACTTACACATCGAAGATTCGGTGGTAGCGGCGGGAGTCCATTCTCCGGACTCAGTTCAATAGCAGTGCGATCTGGC

TCTTATCTGGATGCTATCATAATCGACGGCGTGCACCATGGAGGCTCCGGCGGCAATCTCTCCCCCACTTTCACTTTCGGC

TCTGGAGAGTACATATCCAATATGACAATTAGAAGTGGCGACTATATCGACAATATCTCATTCGAAACCAACCAGGGTCGG

AAATTTGGGCCATATGGAGGATCCGGTGGAAGCGCTAACACACTCAGTAATGTTCGAGTAATCCAGATTAACGGCTCCGCG

GGGGATTACTTGGATTCCCTGGACATATATTATGAGCAGTATTGA

-K NK (SEQ ID NO: 21)

ATGAAAAGCCTGACTCACCGGAGATTCGGGGGCAGCGGCGGTAGCCCTTTTTCCGGGCTGAGCAGCATCGCCGTGCGCTCC

GGGTCTTACCTGGATGCCATAATCATCGACGGGGTGCACCACGGAGGGTCCGGTGGAAATCTTTCACCGACTTTTACATTT

GGATCCGGCGAATACATTTCTAATATGACCATTAGGTCCGGAGACTACATCGATAACATTAGCTTCGAAACGAACCAGGGG

CGGCGCTTTGGACCCTATGGTGGCAGCGGTGGCAGCGCCAACACCCTCAGCAACGTCAGAGTGATCCAGATCAATGGCAGC

GCCGGGGACTACCTGGATAGCCTGGACATCTATTACGAGCAGTACTGA

Figure 6A:
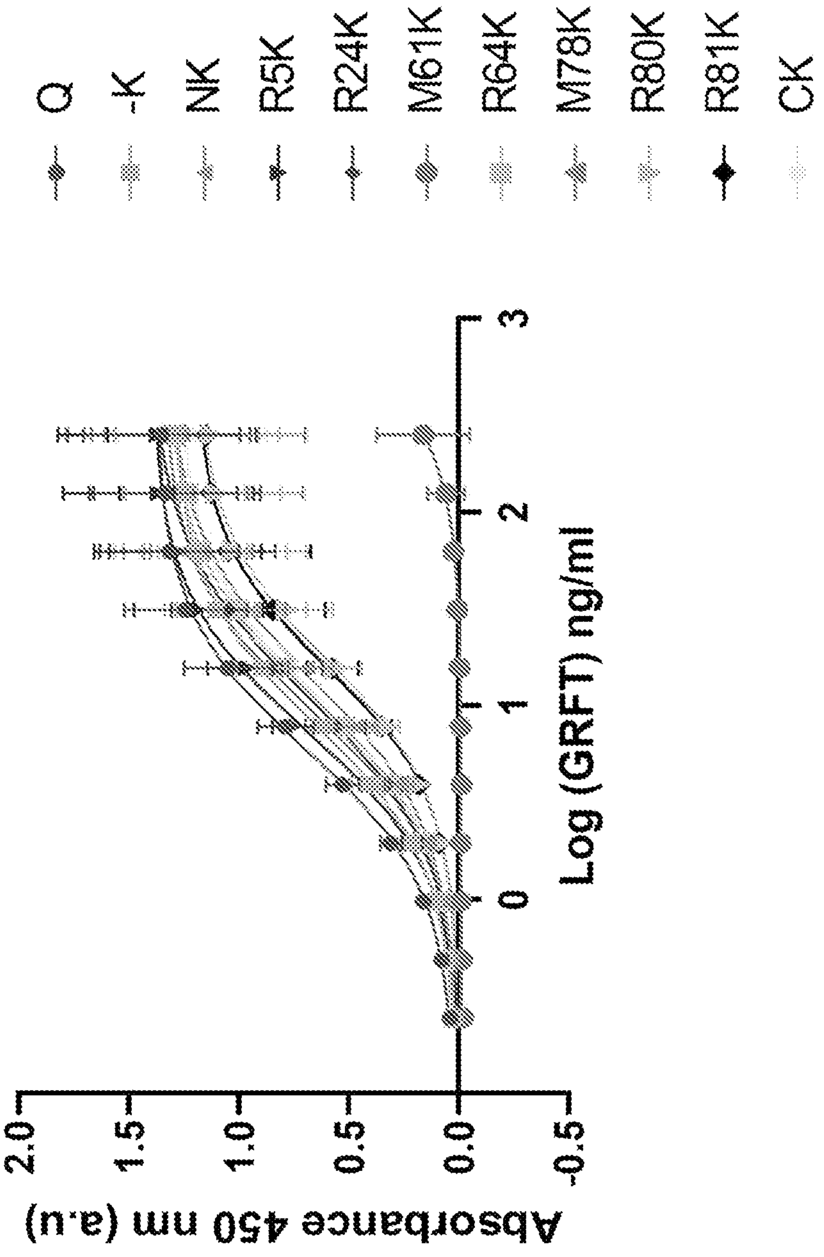
FIG. 6A-6B are graphs showing Gp120 activity of all the non-PEGylated GRFT variants based on absorbance (FIG. 6A) or EC50 (FIG. 6B).
Figure 6B:
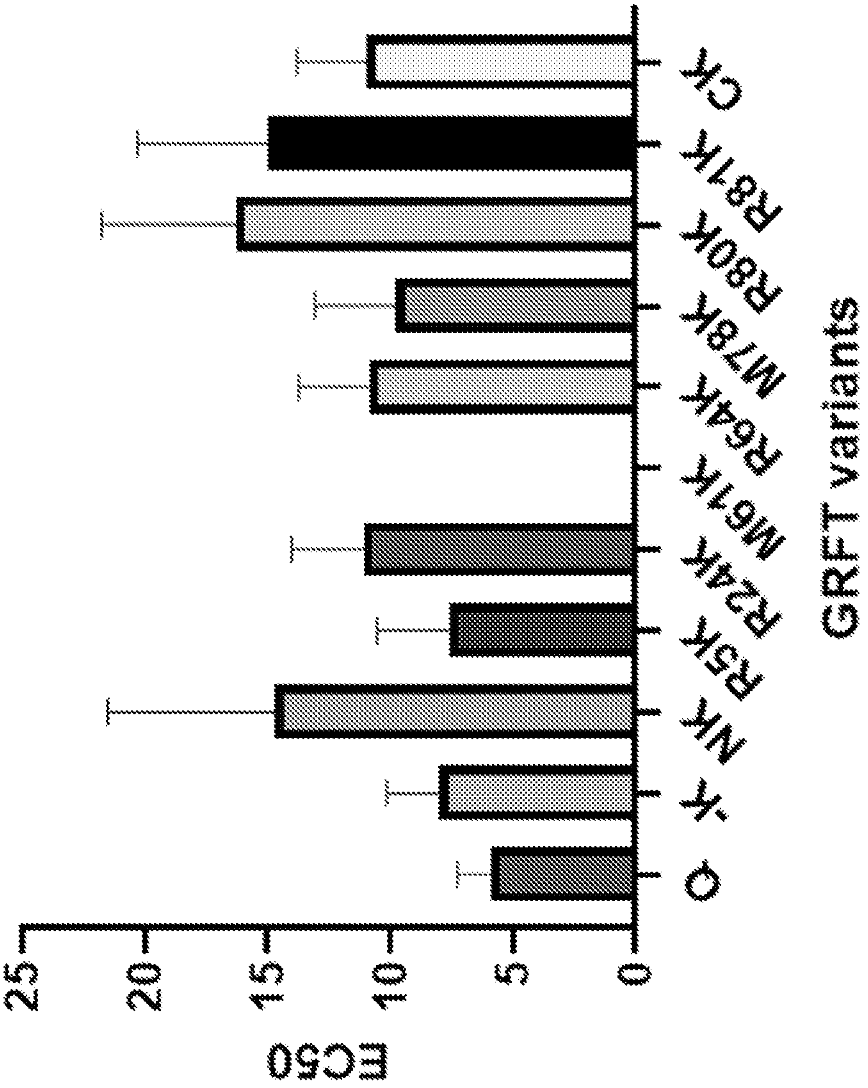
Figure 7A:
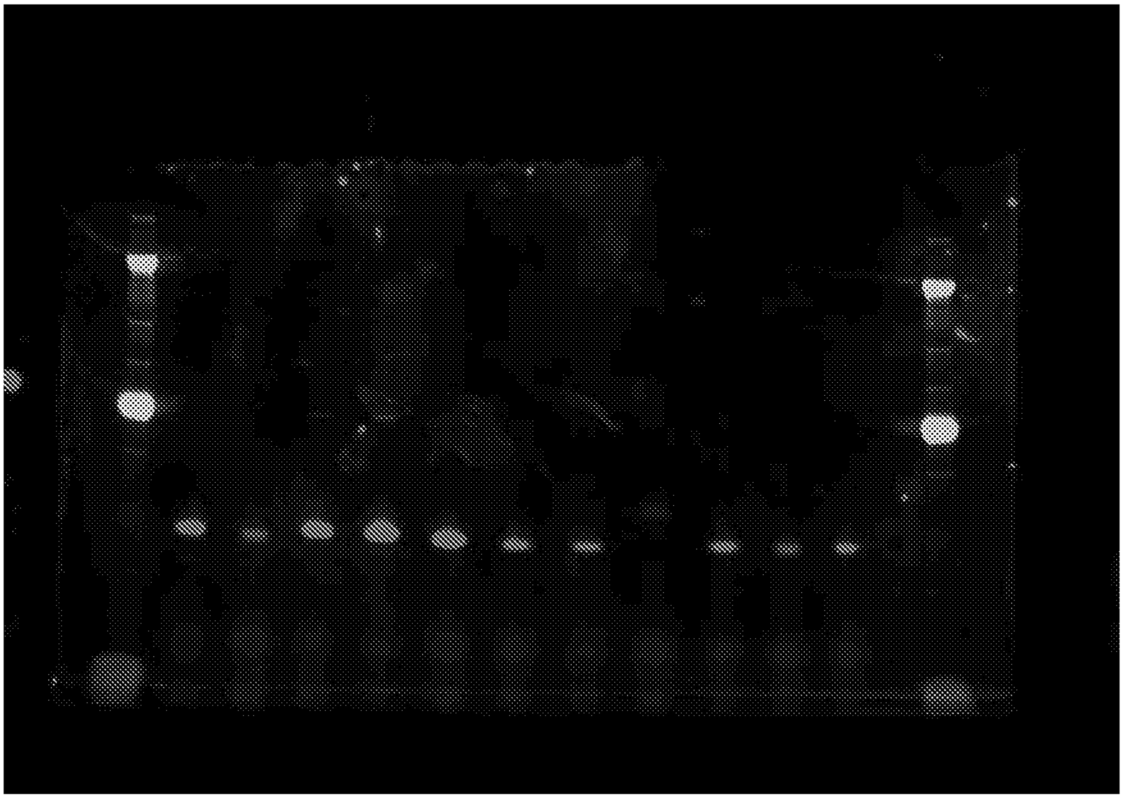
FIG. 7A is a gel showing the fluorescently labeled GRFT variants.
Figure 7B:
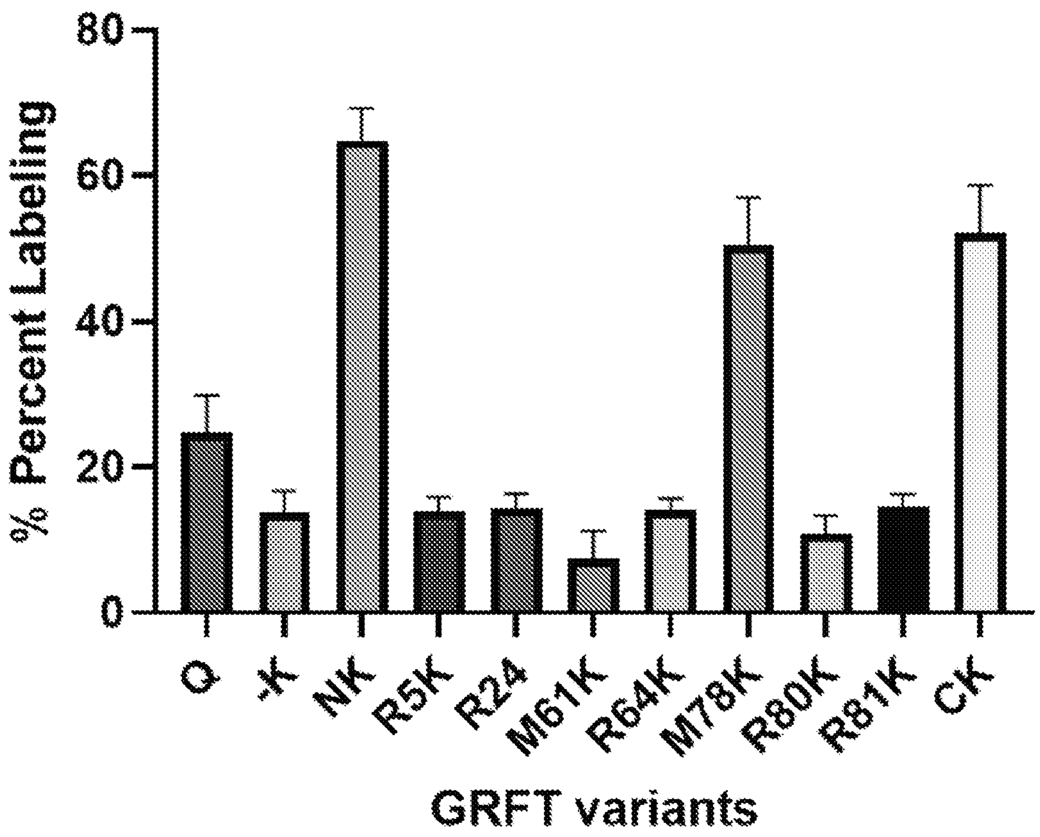
FIG. 7B is a graph showing the amount of fluorescein conjugation.

All of the GRFT variants generated, in the absence of PEGylation, were evaluated for Gp120 activity based on absorbance (FIG. 6A) and their EC50 value (FIG. 6B). In addition, the labeling capacity of the GRFT variants in the absence of PEGylation was assessed (FIGS. 7A and 7B).

The GRFT variants were PEGylated by incubation with a molar excess of 2,000 or 20,000 MW PEG NHS esters in the presence of DMSO overnight at room temperature. DMSO was removed through ultrafiltration and the product was purified through reverse phase chromatography, resulting in retention of products having at least one PEG moiety per dimer. The PEGylated GRFT variants were then concentrated and buffer exchanged into PBS.

Figure 8A:
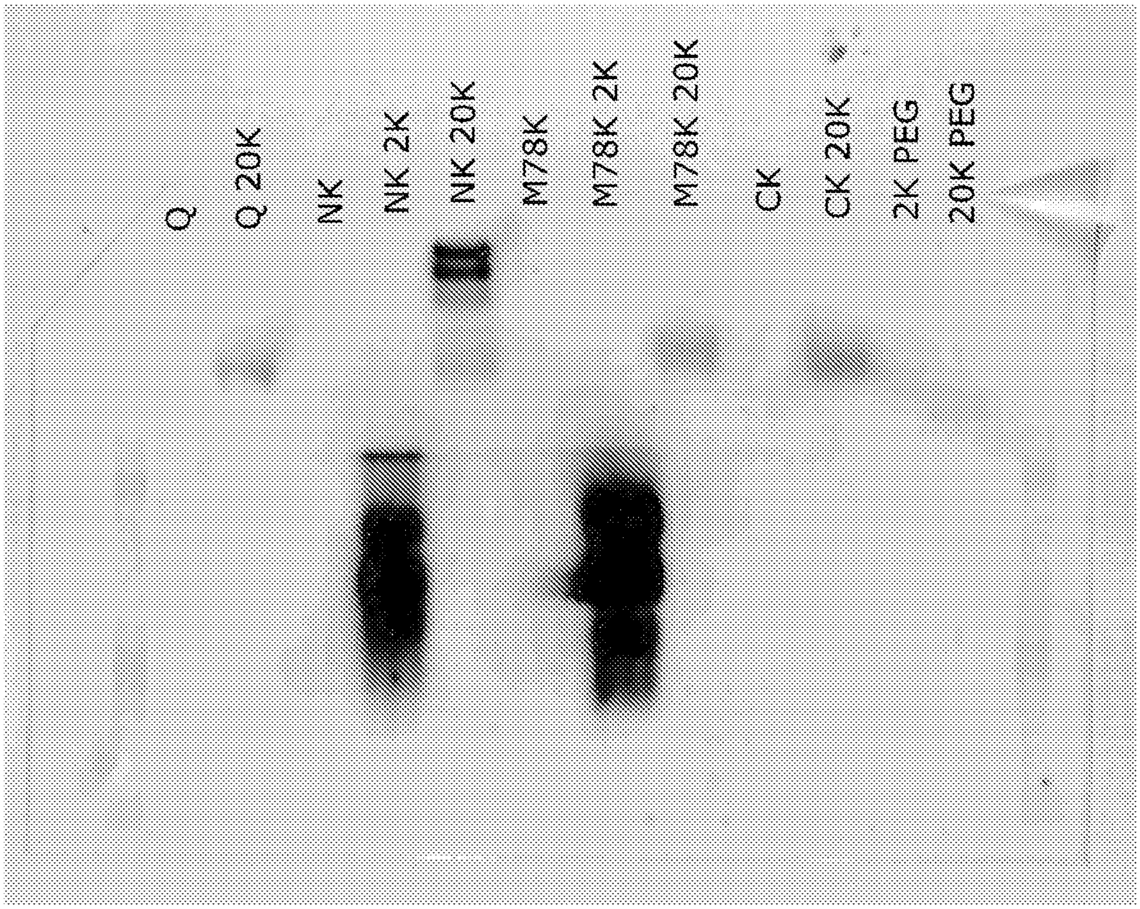
FIG. 8A-8B are photographs of a Western blot probed with anti-PEG antibodies (FIG. 8A) or anti-GRFT antibodies (FIG. 8B).
Figure 8B:
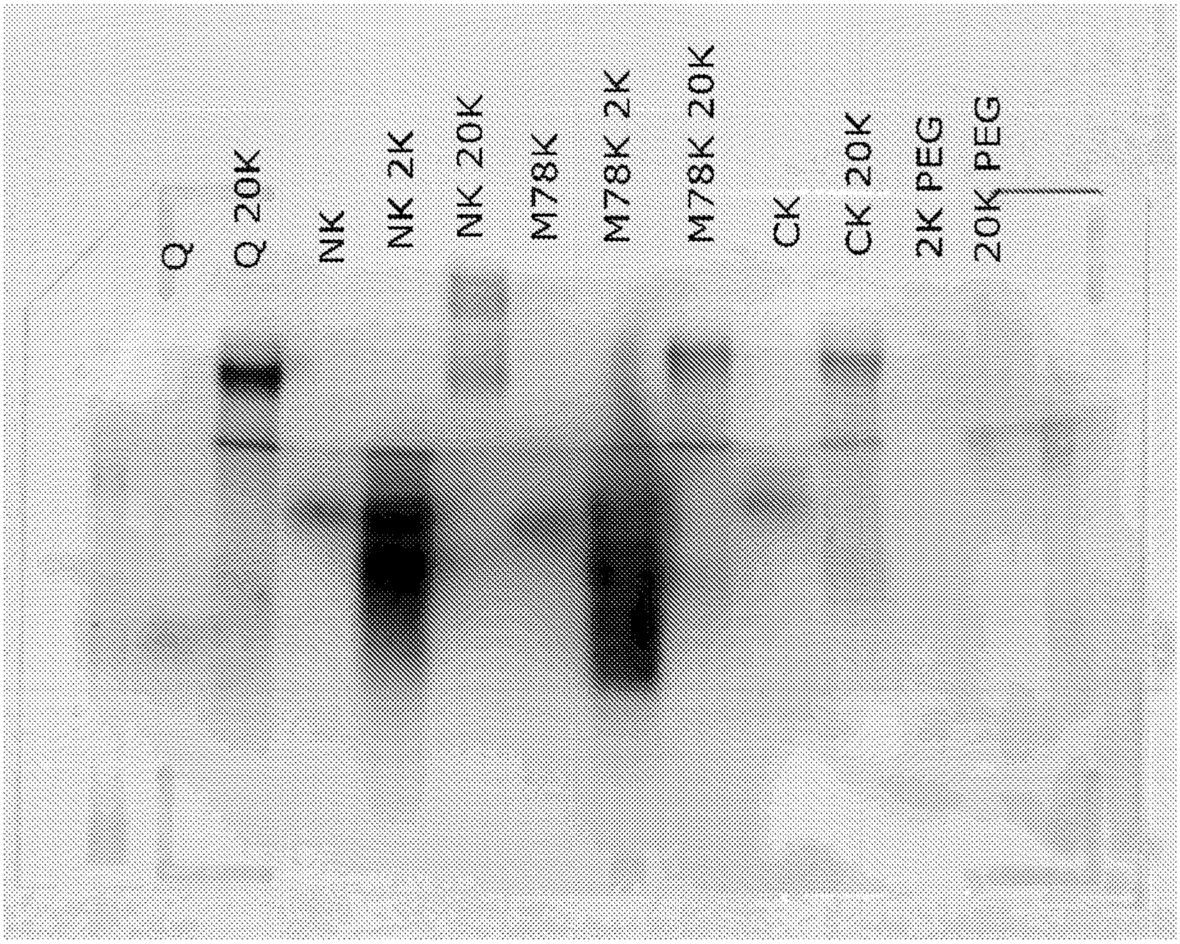
Figure 9:
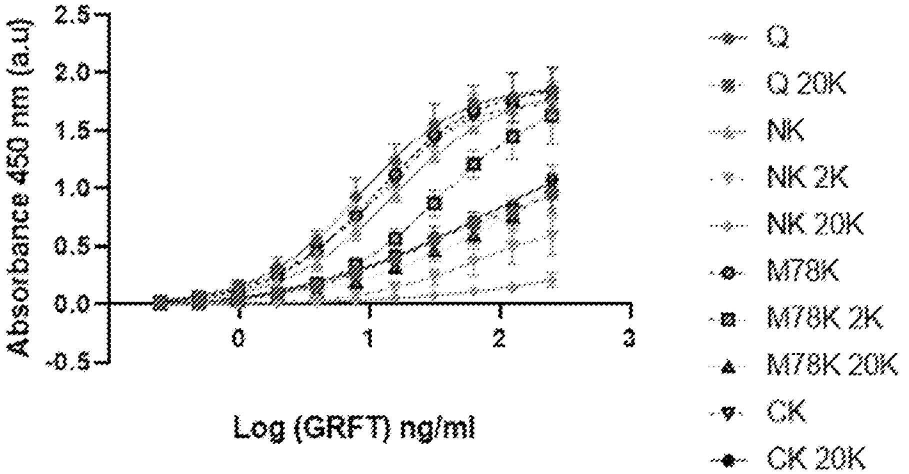
FIG. 9 is a graph showing Gp120 activity of all the PEGylated GRFT variants based on absorbance.
Figure 10A:
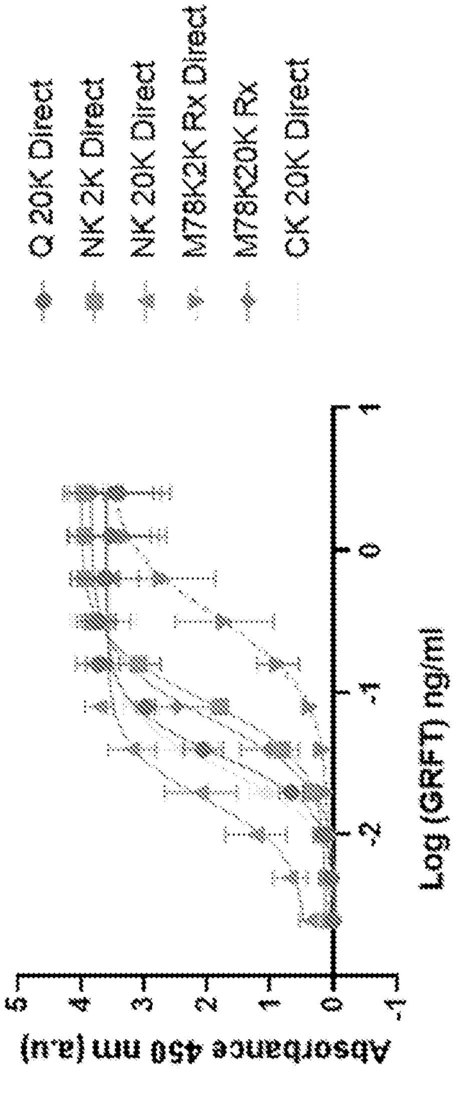
FIG. 10A-10B are graphs showing Gp120 activity of all of the PEGylated GRFT variants using a direct ELISA (FIG. 10A) or an indirect ELISA (FIG. 10B).
Figure 10B:
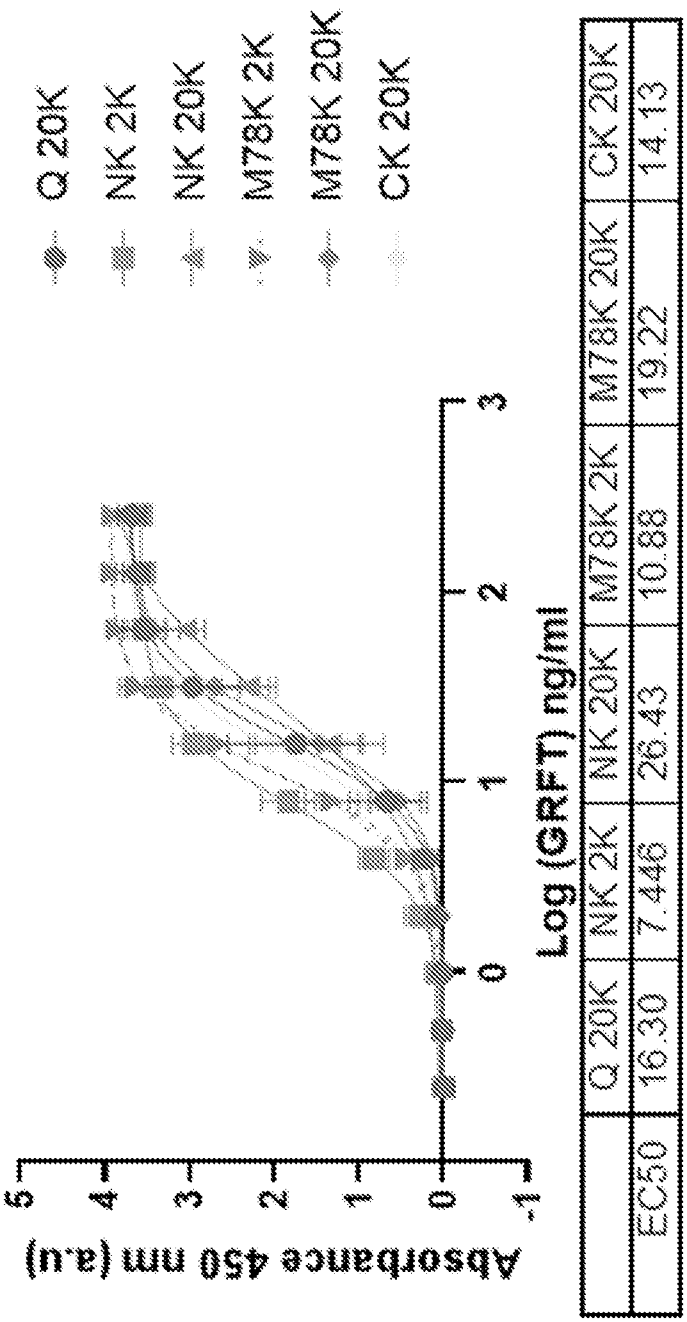

Similarly, the PEGylated GRFT variants were evaluated using Western Blot with an anti-PEG antibody (FIG. 8A) or an anti-GRFT antibody (FIG. 8B). The PEGylated GRFT variants also were evaluated for Gp120 activity (FIG. 9). The Gp120 activity experiments were repeated using a direct anti-PEG ELISA (2.5 µg/ml protein Rx; 0.5 µg/ml primary rabbit anti-PEG antibody; and 0.25 µg/ml second goat anti-rabbit antibody; FIG. 10A) and an indirect anti-PEG ELISA (250 ng/ml BAL Gp120; 250 ng/ml protein Rx; 0.5 µg/ml primary rabbit anti-PEG antibody; and 0.25 µg/ml secondary goat anti-rabbit antibody; FIG. 10B).

The results shown in FIG. 9 replicated the experiment in FIG. 6A but used PEGylated GRFT variants to assess binding to the HIV protein gp120. Binding complexes were detected using GRFT polyclonal antibodies. Some of the lower activity observed in FIG. 9 was attributed to reduced binding activity or reduced availability of antibody binding sites.

FIG. 10A used a direct ELISA to determine relative content of PEG. While not quantitative, these experiments indicated that-K M78K had the highest degree of labeling, meaning the -K M78K variant had the highest amount of conjugated PEGs. FIG. 10B shows the ranking activity of the conjugated variants based upon EC50. The results in FIG. 10B show that the NK variant PEGylated with 20,000 MW PEG exhibited the least activity.

Example 6—Efficacy Against HIV

Figure 11:
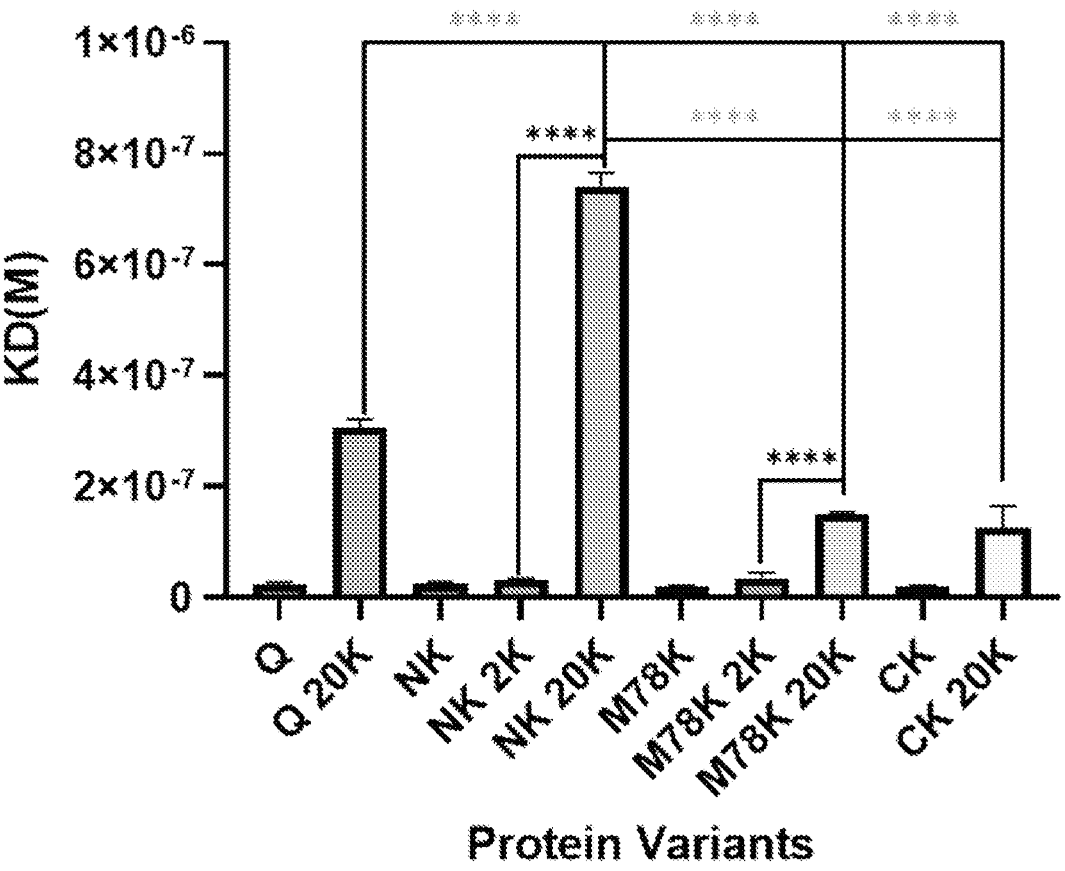
FIG. 11 is a graph showing the affinity to HIV Gp120 by PEGylated vs. non-PEGylated GRFT variants assessed by SPR.

The affinity of the PEGylated GRFT variants for the HIV Gp120 protein compared to the non-PEGylated GRFT variants was assessed using SPR (FIG. 11). The data is shown below in Table 3.

TABLE 3

| Variant | Q | Q 20K | NK | NK 2K | NK 20K | M78K | M78K 2K | M78K 20K | CK | CK 20K |
|---|---|---|---|---|---|---|---|---|---|---|
| Mean KD | 24.1 | 306 | 24.6 | 32.3 | 741 | 18.5 | 34.9 | 150 | 19.4 | 125 |

These experiments demonstrated that, while there is some loss in activity by all conjugation variants, nanomolar affinity for HIV gp120 is retained.

Example 7—Efficacy Against CoV-2

Figure 12:
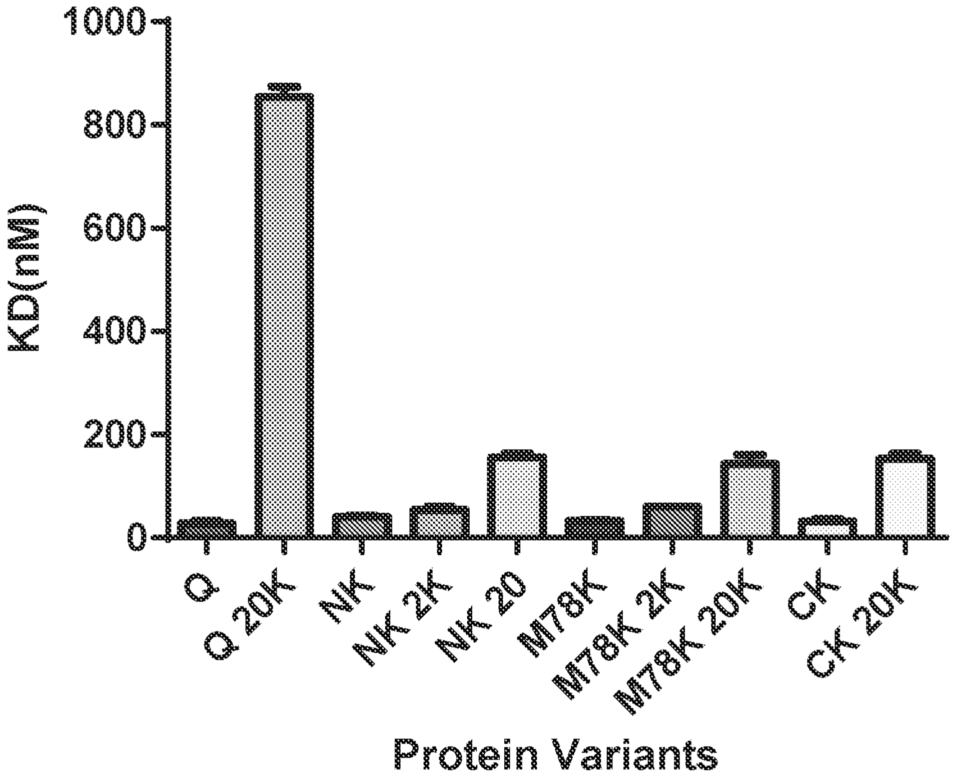
FIG. 12 is a graph showing the affinity to SARS-2 S1 Spike protein by PEGylated vs. non-PEGylated GRFT variants assessed by SPR.
Figures 13A, 13B, 13C, 13D, 13E, 13F:
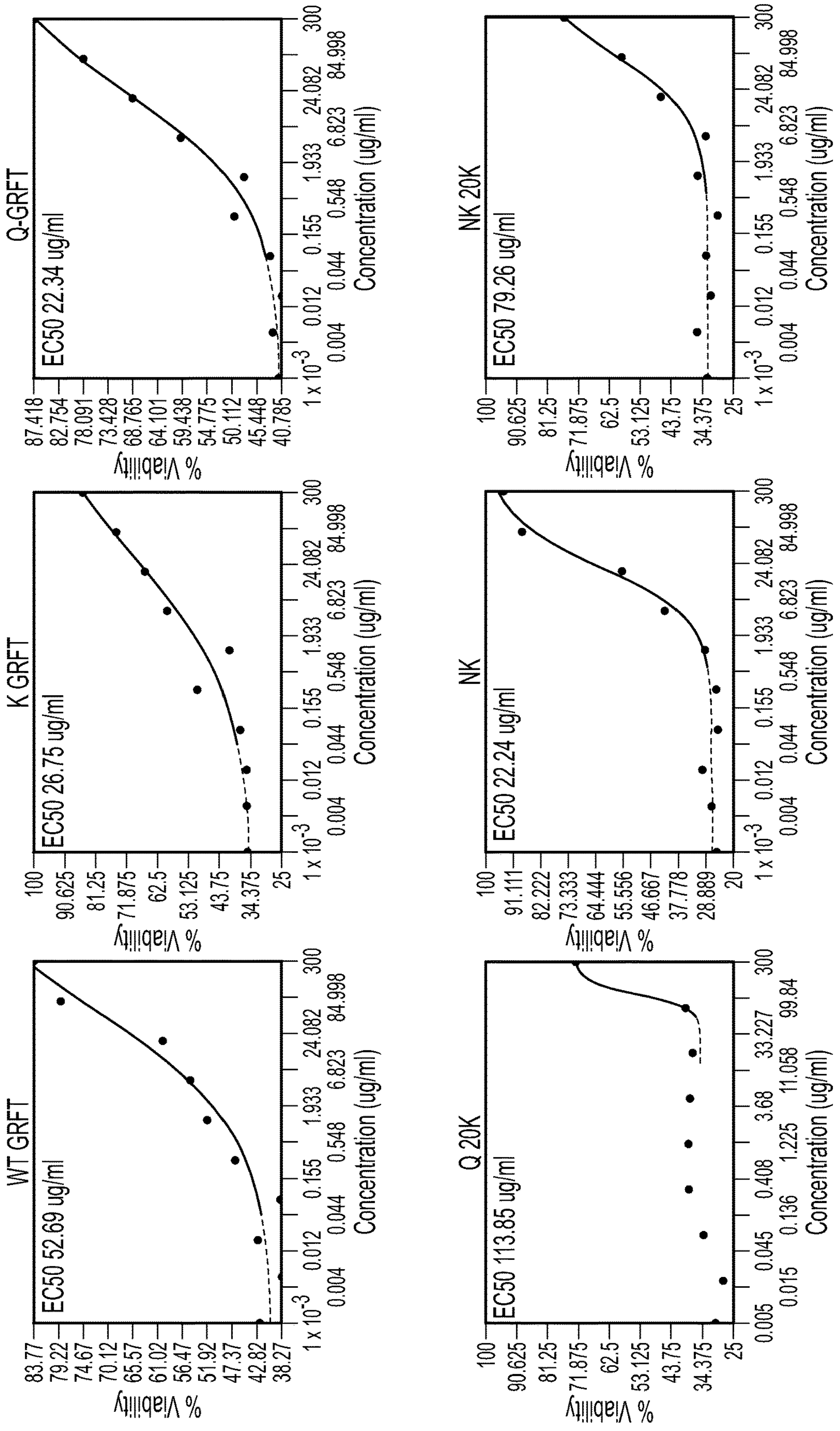
FIG. 13A-13L are graphs showing the EC50 for each of the PEGylated GRFT variants.
Figures 13G, 13H, 13I, 13J, 13K, 13L:
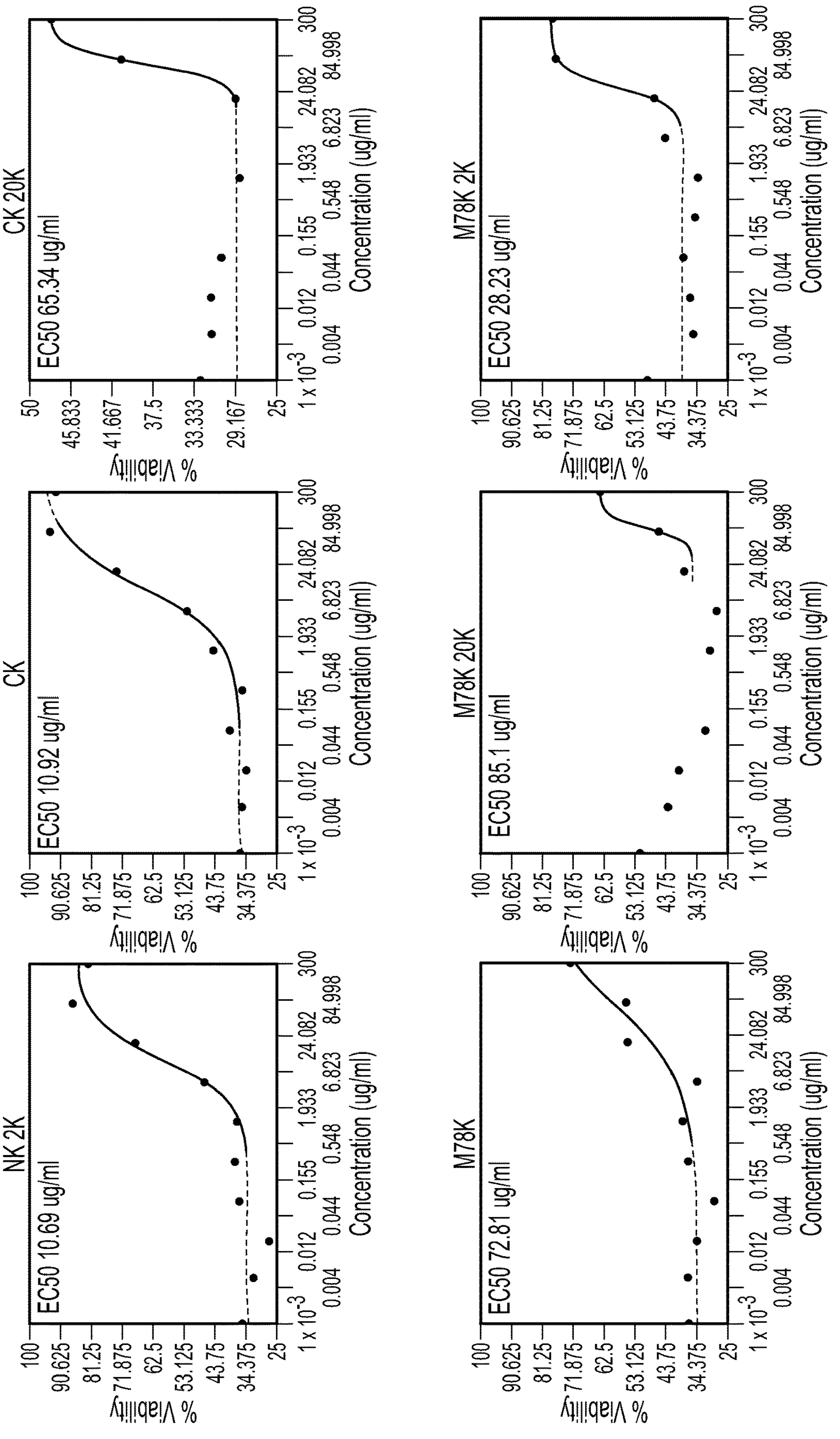

The affinity of the PEGylated GRFT variants for the CoV-2 Spike protein compared to the non-PEGylated GRFT variants was assessed using SPR (FIG. 12). The data is shown below in Table 4.

TABLE 4

| Variant | Q | Q 20K | NK | NK 2K | NK 20K | M78K | M78K 2K | M78K 20K | CK | CK 20K |
|---|---|---|---|---|---|---|---|---|---|---|
| Mean KD | 27.98 | 854.3 | 39.56 | 53.97 | 155.7 | 33.22 | 60.17 | 142.7 | 32.45 | 152.7 |

Micro-neutralization assays for CoV-2 also were performed, and the results are shown in FIG. 13A-FIG. 13L.

These experiments demonstrated that GRFT PEGylation variants maintain binding activity against SARS-COV-2 spike protein and have the capability to neutralize the virus and prevent infection.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A mutant griffithsin (GRFT) polypeptide comprising the amino acid sequence of SEQ ID NO: 1, wherein a lysine is substituted in at least one amino acid position selected from the group consisting of 1, 5, 24, 61, 64, 80, 81, and 122.

2. The mutant GRFT polypeptide of claim 1, comprising the amino acid sequence of SEQ ID NO: 1, wherein a lysine is substituted in at least two amino acid positions selected from the group consisting of 1, 5, 24, 61, 64, 78, 80, 81, and 122.

3. The mutant GRFT polypeptide of claim 1, comprising the amino acid sequence of SEQ ID NO: 1, wherein a lysine is substituted in at least three amino acid positions selected from the group consisting of 1, 5, 24, 61, 64, 78, 80, 81, and 122.

4. A mutant griffithsin (GRFT) polypeptide comprising the amino acid sequence selected from the group consisting of SEQ ID NOs: 3-11, wherein the native lysine at positions 7 and 100 of the GRFT polypeptide comprising the amino acid sequence of SEQ ID NO: 1 has been substituted with arginine and a lysine is respectively substituted in one amino acid position selected from the group consisting of 1, 5, 24, 61, 64, 78, 80, 81, and 122.

5. The mutant GRFT polypeptide of any of claim 1, wherein the GRFT polypeptide comprises polyethylene glycol (PEG) covalently attached to one or more lysine.

6. The mutant GRFT polypeptide of any of claim 1, further comprising a therapeutic moiety covalently attached to the mutant GRFT polypeptide.

7. The mutant GRFT polypeptide of claim 6, wherein the therapeutic moiety is selected from the group consisting of an anti-viral, an anti-microbial, a drug, a small molecule, a therapeutic protein, a nanoparticle, and an enzyme.

8. A nucleic acid molecule comprising the nucleic acid sequence selected from the group consisting of SEQ ID NO: 13-21, encoding the mutant griffithsin (GRFT) polypeptide of claim 4 comprising the amino acid sequence selected from the group consisting of SEQ ID NO: 3-11, wherein the native lysine at positions 7 and 100 of the GRFT polypeptide comprising the amino acid sequence of SEQ ID NO: 1 has been substituted with arginine and a lysine is respectively substituted in one amino acid position selected from the group consisting of 1, 5, 24, 61, 64, 78, 80, 81, and 122.

9. The nucleic acid molecule of claim 8, wherein the nucleic acid encodes the mutant GRFT polypeptide comprising the amino acid sequence of SEQ ID NO: 1 of any of claims 1-3, wherein the codon for lysine is substituted within the nucleic acid molecule corresponding to positions 7 and 100 of the GRFT polypeptide comprising the amino acid sequence of SEQ ID NO: 1, to yield the native lysine at those two positions.

10. A vector comprising the nucleic acid molecule of claim 8.

11. A host cell comprising the nucleic acid molecule of claim 8 or the vector of claim 10.

12. A therapeutic composition comprising the mutant GRFT polypeptide of any of claim 1 and a pharmaceutically acceptable carrier.

13. The therapeutic composition of claim 12, further comprising a therapeutic moiety.

14. The therapeutic composition of claim 13, wherein the therapeutic moiety is selected from the group consisting of an anti-viral, an anti-microbial, a drug, a small molecule, a therapeutic protein, a nanoparticle and an enzyme.

15. The therapeutic composition of any of claim 13 or 14, wherein the therapeutic moiety is covalently attached to the mutant GRFT polypeptide.

16. A method of systematically treating an infection caused by a virus in an individual in need thereof, comprising:

administering a therapeutically effective amount of a mutant griffithsin (GRFT) polypeptide of claim 1 or the therapeutic composition of claim 12 to the individual;

wherein the virus is selected from the group consisting of human immunodeficiency virus (HIV) and coronavirus (SARS-COV).

17. The method of claim 16, wherein the administering step is by a route selected from the group consisting of intraperitoneal, intravenously, subcutaneous, intranasal, intrarectal and sublingual.

18. The method of claim 16, wherein the GRFT polypeptide comprises polyethylene glycol (PEG) covalently attached to one or more lysine.

19. The method of claim 16, wherein the therapeutic composition further comprises a therapeutic moiety.

20. The method of claim 19, wherein the therapeutic moiety is selected from the group consisting of an anti-viral, an anti-microbial, a drug, a small molecule, a therapeutic protein, a nanoparticle, and an enzyme.

21. The method of any one of claim 19 or 20, wherein the therapeutic moiety is covalently attached to the mutant GRFT polypeptide.

* * * * *

SEQUENCE LISTING

```
<160> NUMBER OF SEQ ID NOS: 21

<210> SEQ ID NO 1
<211> LENGTH: 122
<212> TYPE: PRT
<213> ORGANISM: Artificial
<220> FEATURE:
<223> OTHER INFORMATION: synthetic peptide

<400> SEQUENCE: 1

Met Ser Leu Thr His Arg Lys Phe Gly Gly Ser Gly Gly Ser Pro Phe
1               5                   10                  15

Ser Gly Leu Ser Ser Ile Ala Val Arg Ser Gly Ser Tyr Leu Asp Ala
            20                  25                  30
```

-continued

```
Ile Ile Ile Asp Gly Val His His Gly Gly Ser Gly Gly Asn Leu Ser
        35                  40                  45

Pro Thr Phe Thr Phe Gly Ser Gly Glu Tyr Ile Ser Asn Met Thr Ile
    50                  55                  60

Arg Ser Gly Asp Tyr Ile Asp Asn Ile Ser Phe Glu Thr Asn Gln Gly
65                  70                  75                  80

Arg Arg Phe Gly Pro Tyr Gly Gly Ser Gly Gly Ser Ala Asn Thr Leu
                85                  90                  95

Ser Asn Val Lys Val Ile Gln Ile Asn Gly Ser Ala Gly Asp Tyr Leu
            100                 105                 110

Asp Ser Leu Asp Ile Tyr Tyr Glu Gln Tyr
        115                 120


<210> SEQ ID NO 2
<211> LENGTH: 122
<212> TYPE: PRT
<213> ORGANISM: Artificial
<220> FEATURE:
<223> OTHER INFORMATION: synthetic peptide

<400> SEQUENCE: 2

Met Ser Leu Thr His Arg Arg Phe Gly Gly Ser Gly Gly Ser Pro Phe
1               5                   10                  15

Ser Gly Leu Ser Ser Ile Ala Val Arg Ser Gly Ser Tyr Leu Asp Ala
            20                  25                  30

Ile Ile Ile Asp Gly Val His His Gly Gly Ser Gly Gly Asn Leu Ser
        35                  40                  45

Pro Thr Phe Thr Phe Gly Ser Gly Glu Tyr Ile Ser Asn Met Thr Ile
    50                  55                  60

Arg Ser Gly Asp Tyr Ile Asp Asn Ile Ser Phe Glu Thr Asn Gln Gly
65                  70                  75                  80

Arg Arg Phe Gly Pro Tyr Gly Gly Ser Gly Gly Ser Ala Asn Thr Leu
                85                  90                  95

Ser Asn Val Arg Val Ile Gln Ile Asn Gly Ser Ala Gly Asp Tyr Leu
            100                 105                 110

Asp Ser Leu Asp Ile Tyr Tyr Glu Gln Tyr
        115                 120


<210> SEQ ID NO 3
<211> LENGTH: 123
<212> TYPE: PRT
<213> ORGANISM: Artificial
<220> FEATURE:
<223> OTHER INFORMATION: synthetic peptide

<400> SEQUENCE: 3

Met Ser Leu Thr His Arg Arg Phe Gly Gly Ser Gly Gly Ser Pro Phe
1               5                   10                  15

Ser Gly Leu Ser Ser Ile Ala Val Arg Ser Gly Ser Tyr Leu Asp Ala
            20                  25                  30

Ile Ile Ile Asp Gly Val His His Gly Gly Ser Gly Gly Asn Leu Ser
        35                  40                  45

Pro Thr Phe Thr Phe Gly Ser Gly Glu Tyr Ile Ser Asn Met Thr Ile
    50                  55                  60

Arg Ser Gly Asp Tyr Ile Asp Asn Ile Ser Phe Glu Thr Asn Gln Gly
65                  70                  75                  80

Arg Arg Phe Gly Pro Tyr Gly Gly Ser Gly Gly Ser Ala Asn Thr Leu
                85                  90                  95
```

```
Ser Asn Val Arg Val Ile Gln Ile Asn Gly Ser Ala Gly Asp Tyr Leu
            100                 105                 110

Asp Ser Leu Asp Ile Tyr Tyr Glu Gln Tyr Lys
        115                 120


<210> SEQ ID NO 4
<211> LENGTH: 122
<212> TYPE: PRT
<213> ORGANISM: Artificial
<220> FEATURE:
<223> OTHER INFORMATION: synthetic peptide

<400> SEQUENCE: 4

Met Ser Leu Thr His Lys Arg Phe Gly Gly Ser Gly Gly Ser Pro Phe
1               5                   10                  15

Ser Gly Leu Ser Ser Ile Ala Val Arg Ser Gly Ser Tyr Leu Asp Ala
            20                  25                  30

Ile Ile Ile Asp Gly Val His His Gly Gly Ser Gly Gly Asn Leu Ser
        35                  40                  45

Pro Thr Phe Thr Phe Gly Ser Gly Glu Tyr Ile Ser Asn Met Thr Ile
    50                  55                  60

Arg Ser Gly Asp Tyr Ile Asp Asn Ile Ser Phe Glu Thr Asn Gln Gly
65                  70                  75                  80

Arg Arg Phe Gly Pro Tyr Gly Gly Ser Gly Gly Ser Ala Asn Thr Leu
                85                  90                  95

Ser Asn Val Arg Val Ile Gln Ile Asn Gly Ser Ala Gly Asp Tyr Leu
            100                 105                 110

Asp Ser Leu Asp Ile Tyr Tyr Glu Gln Tyr
        115                 120


<210> SEQ ID NO 5
<211> LENGTH: 122
<212> TYPE: PRT
<213> ORGANISM: Artificial
<220> FEATURE:
<223> OTHER INFORMATION: synthetic peptide

<400> SEQUENCE: 5

Met Ser Leu Thr His Arg Arg Phe Gly Gly Ser Gly Gly Ser Pro Phe
1               5                   10                  15

Ser Gly Leu Ser Ser Ile Ala Val Lys Ser Gly Ser Tyr Leu Asp Ala
            20                  25                  30

Ile Ile Ile Asp Gly Val His His Gly Gly Ser Gly Gly Asn Leu Ser
        35                  40                  45

Pro Thr Phe Thr Phe Gly Ser Gly Glu Tyr Ile Ser Asn Met Thr Ile
    50                  55                  60

Arg Ser Gly Asp Tyr Ile Asp Asn Ile Ser Phe Glu Thr Asn Gln Gly
65                  70                  75                  80

Arg Arg Phe Gly Pro Tyr Gly Gly Ser Gly Gly Ser Ala Asn Thr Leu
                85                  90                  95

Ser Asn Val Arg Val Ile Gln Ile Asn Gly Ser Ala Gly Asp Tyr Leu
            100                 105                 110

Asp Ser Leu Asp Ile Tyr Tyr Glu Gln Tyr
        115                 120


<210> SEQ ID NO 6
<211> LENGTH: 122
<212> TYPE: PRT
```

<213> ORGANISM: Artificial
<220> FEATURE:
<223> OTHER INFORMATION: synthetic peptide

<400> SEQUENCE: 6

```
Met Ser Leu Thr His Arg Arg Phe Gly Gly Ser Gly Gly Ser Pro Phe
1               5                   10                  15

Ser Gly Leu Ser Ser Ile Ala Val Arg Ser Gly Ser Tyr Leu Asp Ala
            20                  25                  30

Ile Ile Ile Asp Gly Val His His Gly Gly Ser Gly Gly Asn Leu Ser
        35                  40                  45

Pro Thr Phe Thr Phe Gly Ser Gly Glu Tyr Ile Ser Asn Lys Thr Ile
    50                  55                  60

Arg Ser Gly Asp Tyr Ile Asp Asn Ile Ser Phe Glu Thr Asn Gln Gly
65                  70                  75                  80

Arg Arg Phe Gly Pro Tyr Gly Gly Ser Gly Gly Ser Ala Asn Thr Leu
                85                  90                  95

Ser Asn Val Arg Val Ile Gln Ile Asn Gly Ser Ala Gly Asp Tyr Leu
            100                 105                 110

Asp Ser Leu Asp Ile Tyr Tyr Glu Gln Tyr
        115                 120
```

<210> SEQ ID NO 7
<211> LENGTH: 122
<212> TYPE: PRT
<213> ORGANISM: Artificial
<220> FEATURE:
<223> OTHER INFORMATION: synthetic peptide

<400> SEQUENCE: 7

```
Met Ser Leu Thr His Arg Arg Phe Gly Gly Ser Gly Gly Ser Pro Phe
1               5                   10                  15

Ser Gly Leu Ser Ser Ile Ala Val Arg Ser Gly Ser Tyr Leu Asp Ala
            20                  25                  30

Ile Ile Ile Asp Gly Val His His Gly Gly Ser Gly Gly Asn Leu Ser
        35                  40                  45

Pro Thr Phe Thr Phe Gly Ser Gly Glu Tyr Ile Ser Asn Met Thr Ile
    50                  55                  60

Lys Ser Gly Asp Tyr Ile Asp Asn Ile Ser Phe Glu Thr Asn Gln Gly
65                  70                  75                  80

Arg Arg Phe Gly Pro Tyr Gly Gly Ser Gly Gly Ser Ala Asn Thr Leu
                85                  90                  95

Ser Asn Val Arg Val Ile Gln Ile Asn Gly Ser Ala Gly Asp Tyr Leu
            100                 105                 110

Asp Ser Leu Asp Ile Tyr Tyr Glu Gln Tyr
        115                 120
```

<210> SEQ ID NO 8
<211> LENGTH: 122
<212> TYPE: PRT
<213> ORGANISM: Artificial
<220> FEATURE:
<223> OTHER INFORMATION: synthetic peptide

<400> SEQUENCE: 8

```
Met Ser Leu Thr His Arg Arg Phe Gly Gly Ser Gly Gly Ser Pro Phe
1               5                   10                  15

Ser Gly Leu Ser Ser Ile Ala Val Arg Ser Gly Ser Tyr Leu Asp Ala
            20                  25                  30
```

```
Ile Ile Ile Asp Gly Val His His Gly Gly Ser Gly Gly Asn Leu Ser
        35                  40                  45

Pro Thr Phe Thr Phe Gly Ser Gly Glu Tyr Ile Ser Asn Met Thr Ile
    50                  55                  60

Arg Ser Gly Asp Tyr Ile Asp Asn Ile Ser Phe Glu Thr Asn Lys Gly
65                  70                  75                  80

Arg Arg Phe Gly Pro Tyr Gly Gly Ser Gly Gly Ser Ala Asn Thr Leu
                85                  90                  95

Ser Asn Val Arg Val Ile Gln Ile Asn Gly Ser Ala Gly Asp Tyr Leu
            100                 105                 110

Asp Ser Leu Asp Ile Tyr Tyr Glu Gln Tyr
        115                 120


<210> SEQ ID NO 9
<211> LENGTH: 122
<212> TYPE: PRT
<213> ORGANISM: Artificial
<220> FEATURE:
<223> OTHER INFORMATION: synthetic peptide

<400> SEQUENCE: 9

Met Ser Leu Thr His Arg Arg Phe Gly Gly Ser Gly Gly Ser Pro Phe
1               5                   10                  15

Ser Gly Leu Ser Ser Ile Ala Val Arg Ser Gly Ser Tyr Leu Asp Ala
            20                  25                  30

Ile Ile Ile Asp Gly Val His His Gly Gly Ser Gly Gly Asn Leu Ser
        35                  40                  45

Pro Thr Phe Thr Phe Gly Ser Gly Glu Tyr Ile Ser Asn Met Thr Ile
    50                  55                  60

Arg Ser Gly Asp Tyr Ile Asp Asn Ile Ser Phe Glu Thr Asn Gln Gly
65                  70                  75                  80

Lys Arg Phe Gly Pro Tyr Gly Gly Ser Gly Gly Ser Ala Asn Thr Leu
                85                  90                  95

Ser Asn Val Arg Val Ile Gln Ile Asn Gly Ser Ala Gly Asp Tyr Leu
            100                 105                 110

Asp Ser Leu Asp Ile Tyr Tyr Glu Gln Tyr
        115                 120


<210> SEQ ID NO 10
<211> LENGTH: 122
<212> TYPE: PRT
<213> ORGANISM: Artificial
<220> FEATURE:
<223> OTHER INFORMATION: synthetic peptide

<400> SEQUENCE: 10

Met Ser Leu Thr His Arg Arg Phe Gly Gly Ser Gly Gly Ser Pro Phe
1               5                   10                  15

Ser Gly Leu Ser Ser Ile Ala Val Arg Ser Gly Ser Tyr Leu Asp Ala
            20                  25                  30

Ile Ile Ile Asp Gly Val His His Gly Gly Ser Gly Gly Asn Leu Ser
        35                  40                  45

Pro Thr Phe Thr Phe Gly Ser Gly Glu Tyr Ile Ser Asn Met Thr Ile
    50                  55                  60

Arg Ser Gly Asp Tyr Ile Asp Asn Ile Ser Phe Glu Thr Asn Gln Gly
65                  70                  75                  80

Arg Lys Phe Gly Pro Tyr Gly Gly Ser Gly Gly Ser Ala Asn Thr Leu
```

```
                85                  90                  95

Ser Asn Val Arg Val Ile Gln Ile Asn Gly Ser Ala Gly Asp Tyr Leu
            100                 105                 110

Asp Ser Leu Asp Ile Tyr Tyr Glu Gln Tyr
        115                 120


<210> SEQ ID NO 11
<211> LENGTH: 123
<212> TYPE: PRT
<213> ORGANISM: Artificial
<220> FEATURE:
<223> OTHER INFORMATION: synthetic peptide

<400> SEQUENCE: 11

Met Lys Ser Leu Thr His Arg Arg Phe Gly Gly Ser Gly Gly Ser Pro
1               5                   10                  15

Phe Ser Gly Leu Ser Ser Ile Ala Val Arg Ser Gly Ser Tyr Leu Asp
            20                  25                  30

Ala Ile Ile Ile Asp Gly Val His His Gly Gly Ser Gly Gly Asn Leu
        35                  40                  45

Ser Pro Thr Phe Thr Phe Gly Ser Gly Glu Tyr Ile Ser Asn Met Thr
    50                  55                  60

Ile Arg Ser Gly Asp Tyr Ile Asp Asn Ile Ser Phe Glu Thr Asn Gln
65                  70                  75                  80

Gly Arg Arg Phe Gly Pro Tyr Gly Gly Ser Gly Gly Ser Ala Asn Thr
                85                  90                  95

Leu Ser Asn Val Arg Val Ile Gln Ile Asn Gly Ser Ala Gly Asp Tyr
            100                 105                 110

Leu Asp Ser Leu Asp Ile Tyr Tyr Glu Gln Tyr
        115                 120


<210> SEQ ID NO 12
<211> LENGTH: 369
<212> TYPE: DNA
<213> ORGANISM: Artificial
<220> FEATURE:
<223> OTHER INFORMATION: synthetic nucleic acids

<400> SEQUENCE: 12

atgtcactta cacatcgaag attcggtggt agcggcggga gtccattctc cggactcagt      60

tcaatagcag tgcgatctgg ctcttatctg gatgctatca taatcgacgg cgtgcaccat     120

ggaggctccg gcggcaatct ctcccccact ttcactttcg gctctggaga gtacatatcc     180

aatatgacaa ttagaagtgg cgactatatc gacaatatct cattcgaaac caaccagggt     240

cggcggtttg ggccatatgg aggatccggt ggaagcgcta acacactcag taatgttcga     300

gtaatccaga ttaacggctc cgcgggggat tacttggatt ccctggacat atattatgag     360

cagtattga                                                             369


<210> SEQ ID NO 13
<211> LENGTH: 372
<212> TYPE: DNA
<213> ORGANISM: Artificial
<220> FEATURE:
<223> OTHER INFORMATION: synthetic nucleic acids

<400> SEQUENCE: 13

atgtcactta cacatcgaag attcggtggt agcggcggga gtccattctc cggactcagt      60

tcaatagcag tgcgatctgg ctcttatctg gatgctatca taatcgacgg cgtgcaccat     120
```

ggaggctccg gcggcaatct ctcccccact ttcactttcg gctctggaga gtacatatcc 180
aatatgacaa ttagaagtgg cgactatatc gacaatatct cattcgaaac caaccagggt 240
cggcggtttg ggccatatgg aggatccggt ggaagcgcta acacactcag taatgttcga 300
gtaatccaga ttaacggctc cgcgggggat tacttggatt ccctggacat atattatgag 360
cagtataaat ga 372

<210> SEQ ID NO 14
<211> LENGTH: 369
<212> TYPE: DNA
<213> ORGANISM: Artificial
<220> FEATURE:
<223> OTHER INFORMATION: synthetic nucleic acids

<400> SEQUENCE: 14
atgtcactta cacataaaag attcggtggt agcggcggga gtccattctc cggactcagt 60
tcaatagcag tgcgatctgg ctcttatctg gatgctatca taatcgacgg cgtgcaccat 120
ggaggctccg gcggcaatct ctcccccact ttcactttcg gctctggaga gtacatatcc 180
aatatgacaa ttagaagtgg cgactatatc gacaatatct cattcgaaac caaccagggt 240
cggcggtttg ggccatatgg aggatccggt ggaagcgcta acacactcag taatgttcga 300
gtaatccaga ttaacggctc cgcgggggat tacttggatt ccctggacat atattatgag 360
cagtattga 369

<210> SEQ ID NO 15
<211> LENGTH: 369
<212> TYPE: DNA
<213> ORGANISM: Artificial
<220> FEATURE:
<223> OTHER INFORMATION: synthetic nucleic acids

<400> SEQUENCE: 15
atgtcactta cacatcgaag attcggtggt agcggcggga gtccattctc cggactcagt 60
tcaatagcag tgaagtctgg ctcttatctg gatgctatca taatcgacgg cgtgcaccat 120
ggaggctccg gcggcaatct ctcccccact ttcactttcg gctctggaga gtacatatcc 180
aatatgacaa ttagaagtgg cgactatatc gacaatatct cattcgaaac caaccagggt 240
cggcggtttg ggccatatgg aggatccggt ggaagcgcta acacactcag taatgttcga 300
gtaatccaga ttaacggctc cgcgggggat tacttggatt ccctggacat atattatgag 360
cagtattga 369

<210> SEQ ID NO 16
<211> LENGTH: 369
<212> TYPE: DNA
<213> ORGANISM: Artificial
<220> FEATURE:
<223> OTHER INFORMATION: synthetic nucleic acids

<400> SEQUENCE: 16
atgtcactta cacatcgaag attcggtggt agcggcggga gtccattctc cggactcagt 60
tcaatagcag tgcgatctgg ctcttatctg gatgctatca taatcgacgg cgtgcaccat 120
ggaggctccg gcggcaatct ctcccccact ttcactttcg gctctggaga gtacatatcc 180
aataagacaa ttagaagtgg cgactatatc gacaatatct cattcgaaac caaccagggt 240
cggcggtttg ggccatatgg aggatccggt ggaagcgcta acacactcag taatgttcga 300
gtaatccaga ttaacggctc cgcgggggat tacttggatt ccctggacat atattatgag 360
cagtattga 369

<210> SEQ ID NO 17
<211> LENGTH: 369
<212> TYPE: DNA
<213> ORGANISM: Artificial
<220> FEATURE:
<223> OTHER INFORMATION: synthetic nucleic acids

<400> SEQUENCE: 17
atgtcactta cacatcgaag attcggtggt agcggcggga gtccattctc cggactcagt 60
tcaatagcag tgcgatctgg ctcttatctg gatgctatca taatcgacgg cgtgcaccat 120
ggaggctccg gcggcaatct ctcccccact ttcactttcg gctctggaga gtacatatcc 180
aatatgacaa ttaagagtgg cgactatatc gacaatatct cattcgaaac caaccagggt 240
cggcggtttg ggccatatgg aggatccggt ggaagcgcta acacactcag taatgttcga 300
gtaatccaga ttaacggctc cgcgggggat tacttggatt ccctggacat atattatgag 360
cagtattga 369

<210> SEQ ID NO 18
<211> LENGTH: 369
<212> TYPE: DNA
<213> ORGANISM: Artificial
<220> FEATURE:
<223> OTHER INFORMATION: synthetic nucleic acids

<400> SEQUENCE: 18
atgtcactta cacatcgaag attcggtggt agcggcggga gtccattctc cggactcagt 60
tcaatagcag tgcgatctgg ctcttatctg gatgctataa ttatcgacgg agtacatcac 120
ggggggtctg ggggaaatct ttcaccgact tttacatttg gatccggcga atacatttct 180
aatatgacca ttaggtccgg agactacatc gataacatta gcttcgaaac gaacaagggg 240
cggcgctttg gaccctatgg tggcagcggt ggcagcgcca acaccctcag caacgtcaga 300
gtgatccaga tcaatggcag cgccggggac tacctggata gcctggacat ctattacgag 360
cagtactga 369

<210> SEQ ID NO 19
<211> LENGTH: 369
<212> TYPE: DNA
<213> ORGANISM: Artificial
<220> FEATURE:
<223> OTHER INFORMATION: synthetic nucleic acids

<400> SEQUENCE: 19
atgtcactta cacatcgaag attcggtggt agcggcggga gtccattctc cggactcagt 60
tcaatagcag tgcgatctgg ctcttatctg gatgctatca taatcgacgg cgtgcaccat 120
ggaggctccg gcggcaatct ctcccccact ttcactttcg gctctggaga gtacatatcc 180
aatatgacaa ttagaagtgg cgactatatc gacaatatct cattcgaaac caaccagggt 240
aaacggtttg ggccatatgg aggatccggt ggaagcgcta acacactcag taatgttcga 300
gtaatccaga ttaacggctc cgcgggggat tacttggatt ccctggacat atattatgag 360
cagtattga 369

<210> SEQ ID NO 20
<211> LENGTH: 369

-continued

```
<212> TYPE: DNA
<213> ORGANISM: Artificial
<220> FEATURE:
<223> OTHER INFORMATION: synthetic nucleic acids

<400> SEQUENCE: 20

atgtcactta cacatcgaag attcggtggt agcggcggga gtccattctc cggactcagt     60

tcaatagcag tgcgatctgg ctcttatctg gatgctatca taatcgacgg cgtgcaccat    120

ggaggctccg gcggcaatct ctcccccact ttcactttcg gctctggaga gtacatatcc    180

aatatgacaa ttagaagtgg cgactatatc gacaatatct cattcgaaac caaccagggt    240

cggaaatttg ggccatatgg aggatccggt ggaagcgcta acacactcag taatgttcga    300

gtaatccaga ttaacggctc cgcgggggat tacttggatt ccctggacat atattatgag    360

cagtattga                                                             369


<210> SEQ ID NO 21
<211> LENGTH: 372
<212> TYPE: DNA
<213> ORGANISM: Artificial
<220> FEATURE:
<223> OTHER INFORMATION: synthetic nucleic acids

<400> SEQUENCE: 21

atgaaaagcc tgactcaccg gagattcggg ggcagcggcg gtagcccttt ttccgggctg     60

agcagcatcg ccgtgcgctc cgggtcttac ctggatgcca taatcatcga cggggtgcac    120

cacggagggt ccggtggaaa tctttcaccg acttttacat ttggatccgg cgaatacatt    180

tctaatatga ccattaggtc cggagactac atcgataaca ttagcttcga aacgaaccag    240

gggcggcgct ttggacccta tggtggcagc ggtggcagcg ccaacaccct cagcaacgtc    300

agagtgatcc agatcaatgg cagcgccggg gactacctgg atagcctgga catctattac    360

gagcagtact ga                                                         372
```